United States Patent
Jermy et al.

(10) Patent No.: US 12,144,823 B2
(45) Date of Patent: Nov. 19, 2024

(54) POROUS SILICATE AND/OR ALUMINOSILICATE MATRIX/CERIUM OXIDE NANOPARTICLE NANOCARRIER FOR COMBINATION ANTI-CANCER THERAPEUTIC AND ANTIOXIDANT DELIVERY

(71) Applicant: Imam Abdulrahman Bin Faisal University, Dammam (SA)

(72) Inventors: B. Rabindran Jermy, Dammam (SA); Vijaya Ravinayagam, Dammam (SA); Sarah Almofty, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 49 days.

(21) Appl. No.: 17/731,905

(22) Filed: Apr. 28, 2022

(65) Prior Publication Data
US 2023/0346833 A1    Nov. 2, 2023

(51) Int. Cl.
| | | |
|---|---|---|
| *A61K 33/243* | (2019.01) | |
| *A61K 9/14* | (2006.01) | |
| *A61K 31/12* | (2006.01) | |
| *A61K 31/122* | (2006.01) | |
| *A61K 31/282* | (2006.01) | |
| *A61K 31/352* | (2006.01) | |
| *A61K 31/7048* | (2006.01) | |
| *A61K 47/02* | (2006.01) | |
| *A61P 35/00* | (2006.01) | |

(52) U.S. Cl.
CPC .............. *A61K 33/243* (2019.01); *A61K 9/14* (2013.01); *A61K 31/12* (2013.01); *A61K 31/122* (2013.01); *A61K 31/282* (2013.01); *A61K 31/352* (2013.01); *A61K 31/7048* (2013.01); *A61K 47/02* (2013.01); *A61P 35/00* (2018.01)

(58) Field of Classification Search
CPC .. A61K 33/243; A61K 31/122; A61K 31/282; A61P 35/00
See application file for complete search history.

(56) References Cited

U.S. PATENT DOCUMENTS

| | | | |
|---|---|---|---|
| 10,286,075 B2 | 5/2019 | Townley et al. | |
| 10,478,492 B2 | 11/2019 | Kolb et al. | |
| 2008/0072705 A1* | 3/2008 | Chaumonnot | B01J 23/745 428/550 |
| 2015/0246819 A1* | 9/2015 | Brichka | C01B 33/26 428/328 |
| 2017/0202965 A1* | 7/2017 | Baker | A61K 33/243 |
| 2019/0153279 A1* | 5/2019 | Tawarazako | H01L 21/304 |
| 2020/0281864 A1* | 9/2020 | Jermy | A61K 41/00 |
| 2020/0338122 A1 | 10/2020 | Jermy et al. | |

FOREIGN PATENT DOCUMENTS

| | | |
|---|---|---|
| TW | I625137 B | 6/2018 |
| WO | 2021/011496 A1 | 1/2021 |

OTHER PUBLICATIONS

Dasari et al. "Pharmacology Effects of Cisplatin Combination with Natural Products in Cancer Chemotherapy." Int. J. Mol. Sci., Jan. 28, 2022, 23(1532): 1-25. (Year: 2022).*
Brichka et al. "Anticorrosion Properties of CeO2-Modified Aluminosilicate Nanotubes," 2013, 49(6): 581-585. (Year: 2013).*
Harini, et al. ; An ingenious non-spherical mesoporous silica nanoparticle cargo with curcumin induces mitochondria-mediated apoptosis in breast cancer (MCF-7) cells ; Oncotarget, vol. 10, No. 11 ; pp. 1193-1208 ; Feb. 5, 2019.
Singh, et al. ; Combinatory Cancer Therapeutics with Nanoceria-Capped Mesoporous Silica Nanocarriers through pH-triggered Drug Release and Redox Activity ; ACS Appl Mater Interfaces 9;11 ; pp. 288-299 ; 2019 ; Abstract Only.
Saifi, et al. ; Protective Effect of Nanoceria on Cisplatin-Induced Nephrotoxicity by Amelioration of Oxidative Stress and Pro-inflammatory Mechnisms ; Biological Trace Element Research, vol. 189 ; pp. 145-156 ; Jul. 25, 2018 ; Abstract Only.

* cited by examiner

*Primary Examiner* — Doan T Phan
(74) *Attorney, Agent, or Firm* — Oblon, McClelland, Maier & Neustadt, L.L.P.

(57) ABSTRACT

A nanomedicinal composition comprising a nanocarrier and a pharmaceutical agent mixture including an anti-cancer therapeutic and an antioxidant. The nanocarrier contains a porous silicate and/or aluminosilicate matrix and cerium oxide nanoparticles in the pores of the porous silicate and/or aluminosilicate matrix. The pharmaceutical agent mixture is disposed in the pores and/or on the surface of the nanocarrier by a solution phase impregnation process. The nanomedicinal composition is used in a method of treating breast cancer.

18 Claims, 17 Drawing Sheets

FIG. 10M.    FIG. 10N.
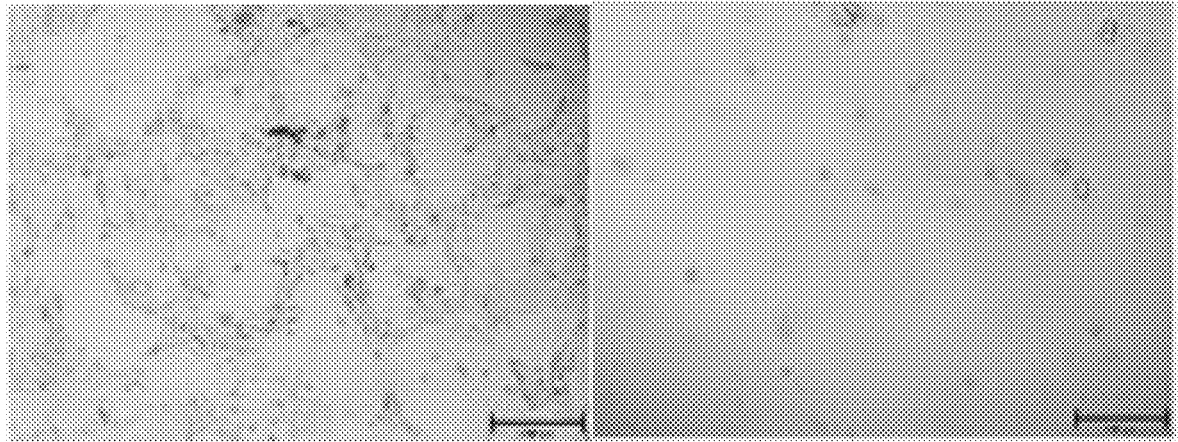
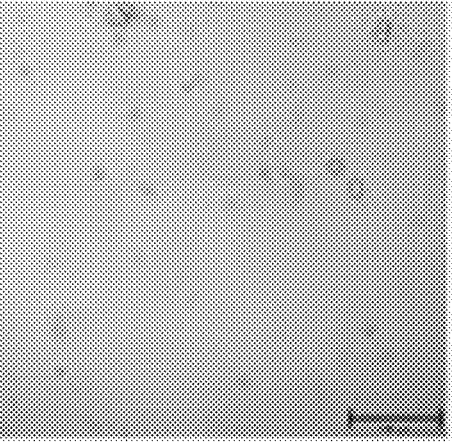
FIG. 11A.    FIG. 11B.
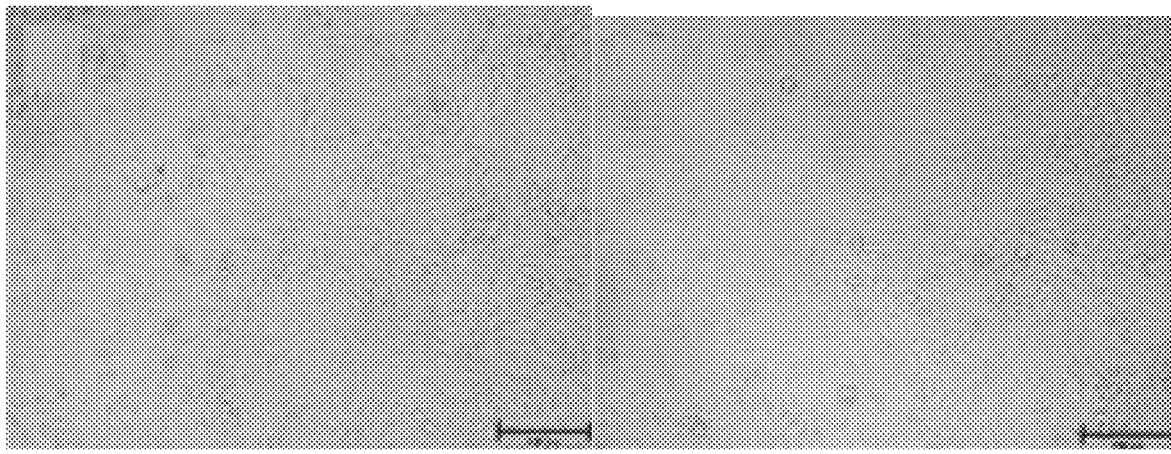
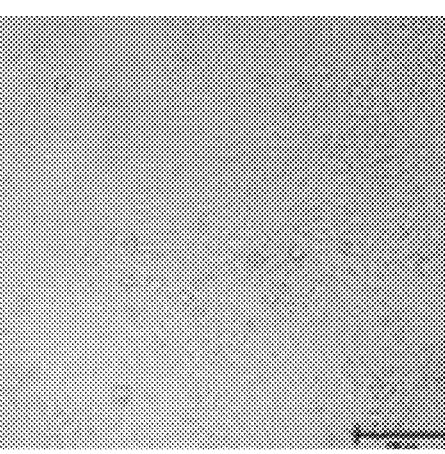
FIG. 11C.    FIG. 11D.
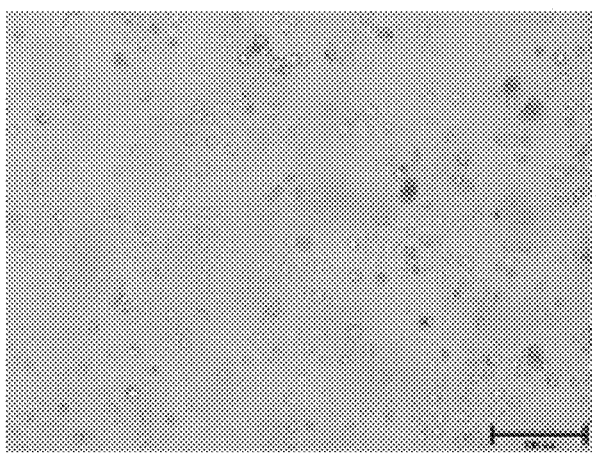
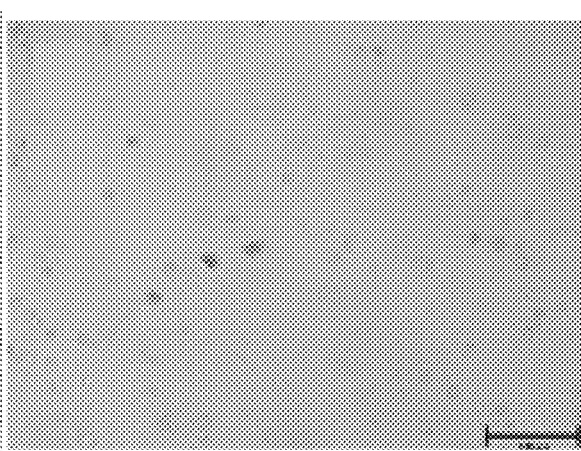

FIG. 11E.
FIG. 11F.
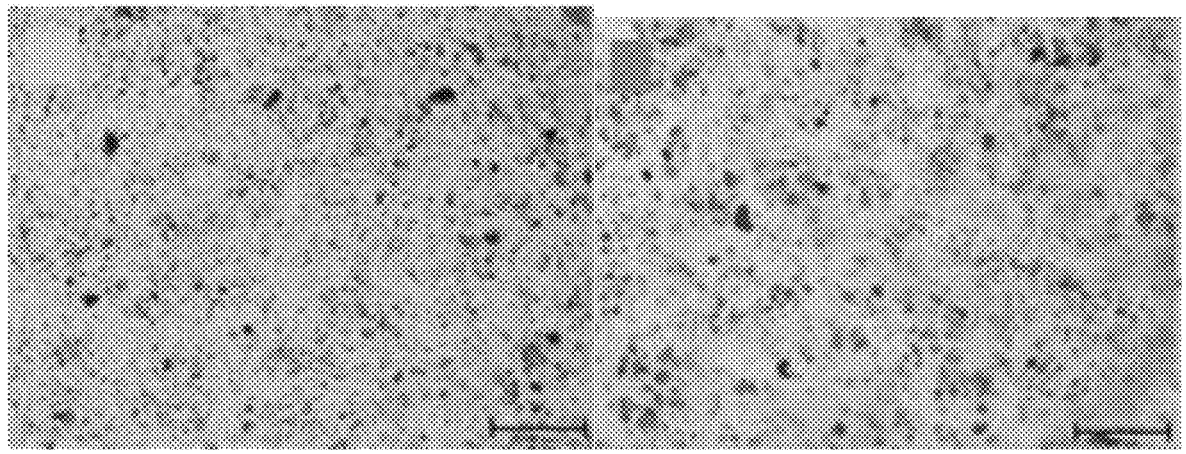
FIG. 11G.
FIG. 11H.
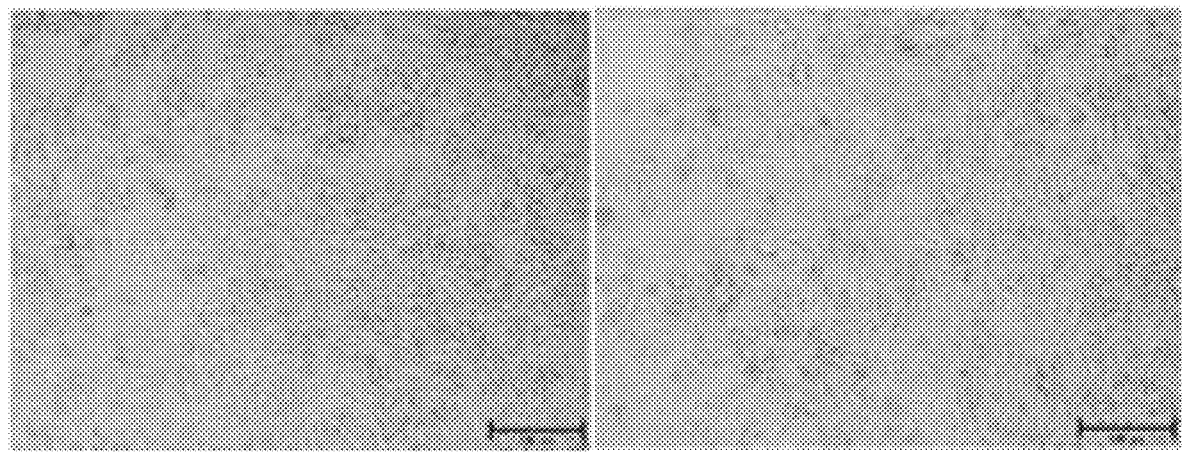
FIG. 11I.
FIG. 11J.
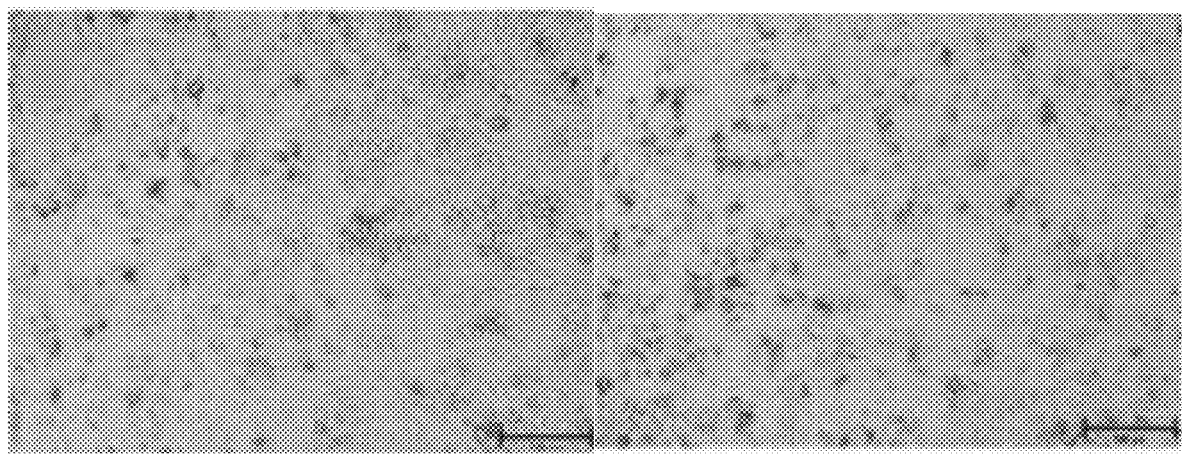

FIG. 11K.
FIG. 11L.
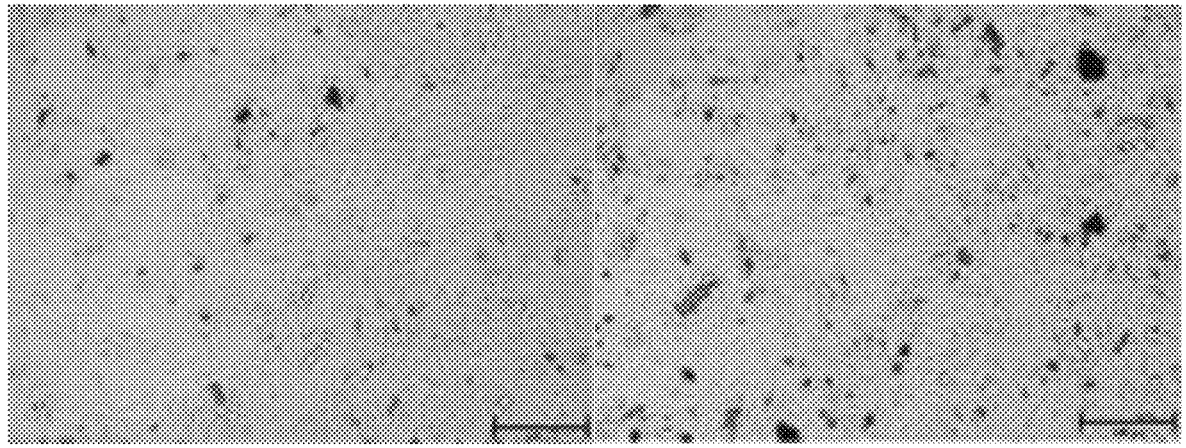
FIG. 11M.
FIG. 11N.
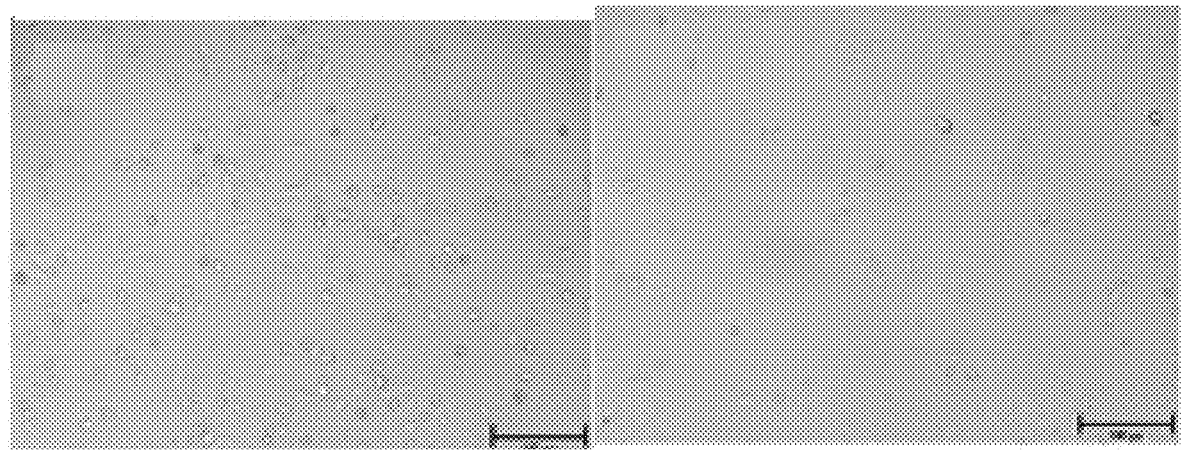

POROUS SILICATE AND/OR ALUMINOSILICATE MATRIX/CERIUM OXIDE NANOPARTICLE NANOCARRIER FOR COMBINATION ANTI-CANCER THERAPEUTIC AND ANTIOXIDANT DELIVERY

BACKGROUND OF THE INVENTION

Field of the Invention

The present disclosure relates to a nanomedicinal composition comprising a nanocarrier, which comprises a porous silicate and/or an, aluminosilicate matrix, and cerium oxide nanoparticles disposed in the pores of the porous silicate and/or the aluminosilicate matrix, and a pharmaceutical agent mixture comprising a platinum (II) complex and an antioxidant disposed in the pores and/or on the surface of the nanocarrier, as well as a method of making the nanomedicinal composition and a method of treating cancer using the nanomedicinal composition.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Treatments for cancers such as cervical cancer and colorectal cancer may include surgery, radiation therapy, chemotherapy, or targeted therapy. However, a continued high mortality of cancer patients reveals shortcomings of such treatments. Also, during cancer treatment, the immunity of the patient is compromised and as a result, the patient is more susceptible to bacterial infections. Conventionally, pharmaceutical compositions are used for cancer and microbial treatments. However, conventional compositions suffer from drawbacks such as poor selectivity between cancerous and non-cancerous cells.

In recent years metal complexes are being increasingly used as drugs for selective delivery of the drug to cancerous cells. However, an excessive concentration of metal ions in the patient affects non-cancerous cells and causes drug induced toxicity. Hence, delivery of agents capable of inducing toxicity to cancerous cells while preventing the non-cancerous cells from the adverse effects of metal complexes is highly desirable.

In view of the foregoing, an objective of the present invention is to provide a nanomedicinal composition comprising a nanocarrier and a pharmaceutical agent mixture comprising an anti-cancer therapeutic and an antioxidant which are disposed within pores and/or on the surface of the nanocarrier. The nanocarrier incorporates a porous silicate and/or aluminosilicate matrix and cerium oxide nanoparticles.

SUMMARY OF THE INVENTION

The present disclosure relates to a nanomedicinal composition comprising a nanocarrier comprising a porous silicate and/or aluminosilicate matrix and cerium oxide nanoparticles having a mean particle size of 1 to 20 nm disposed on the porous silicate and/or aluminosilicate matrix, and a pharmaceutical agent mixture comprising a platinum (II) complex and an antioxidant, the pharmaceutical agent mixture being disposed in the pores and/or on a surface of the nanocarrier.

In some embodiments, the porous silicate and/or aluminosilicate matrix is at least one selected from the group consisting of mesoporous silica spheres and halloysite nanotubes.

In some embodiments, the porous silicate and/or aluminosilicate matrix is particles of mesoporous silica which are substantially spherical and have a mean particle size of 50 to 110 nanometer (nm).

In some embodiments, the porous silicate and/or aluminosilicate matrix is particles of mesoporous silica and the nanocarrier has a surface area of 15 to 45 $m^2/g$, a pore volume of 0.05 to 0.25 $cm^3/g$, and a mean pore size of 14 to 30 nm.

In some embodiments, the porous silicate and/or aluminosilicate matrix is halloysite nanotubes having a mean nanotube outer diameter of 10 to 125 nm and a mean nanotube length of 0.25 to 7.5 μm.

In some embodiments, the porous silicate and/or aluminosilicate matrix is halloysite nanotubes and the nanocarrier has a surface area of 40 to 100 $m^2/g$, a pore volume of 0.15 to 0.37 $cm^3/g$, and a mean pore size of 10 to 22 nm.

In some embodiments, the cerium oxide nanoparticles are present in an amount of 1 to 10 wt % based on a total weight of the nanocarrier.

In some embodiments, the platinum (II) complex is at least one selected from the group consisting of cisplatin, carboplatin, and oxaliplatin.

In some embodiments, the platinum (II) complex is cisplatin.

In some embodiments, the antioxidant is at least one selected from the group consisting of quercetin, rutin, coenzyme Q10, gallic acid and curcumin.

In some embodiments, the antioxidant is curcumin.

In some embodiments, the pharmaceutical agent mixture has a weight ratio of the antioxidant to the platinum (II) complex of 1:1 to 10:1.

In some embodiments, the pharmaceutical agent mixture is present in the nanomedicinal composition in an amount of 5 to 50 wt %, based on a total weight of nanomedicinal composition.

In some embodiments, the nanomedicinal composition releases greater than 15% of a total weight of platinum (II) complex within 6 to 12 hours of contact with a suitable biological medium.

The present disclosure also relates to a method of forming the nanomedicinal composition, the method comprising mixing a cerium salt with the porous silicate and/or aluminosilicate matrix to form a powdery mixture, calcining the powdery mixture to form the nanocarrier, mixing the nanocarrier and the antioxidant in an impregnation solution thereby forming an antioxidant-loaded nanocarrier, and mixing the antioxidant-loaded nanocarrier and the platinum (II) complex in an aqueous solution thereby forming the nanomedicinal composition.

In some embodiments, the calcining is performed at a temperature of 200 to 500° C. for 1 to 10 hours.

In some embodiments, the impregnation solution comprises an alcohol having 1 to 5 carbon atoms and the antioxidant is present in an amount of 1 to 7.5 mg/mL of impregnation solution.

In some embodiments, the aqueous solution is a saline and the platinum (II) complex is present in the aqueous solution at a concentration of 0.5 to 5 mg/mL of aqueous solution.

The present disclosure also relates to a method for treating a cancer in a subject, comprising administering to a subject in need of therapy a pharmaceutical composition comprising the nanomedicinal composition, wherein the cancer is at least one selected from the group consisting of breast cancer, colorectal cancer, and lung cancer.

In some embodiments, the cancer is a breast cancer

BRIEF DESCRIPTION OF THE DRAWINGS

FIG. 5A is $CeO_2$/Silica/Cp/Cur composite at low magnification, FIG. 5B is $CeO_2$/Silica/Cp/Cur composite at low magnification, FIG. 5C is $CeO_2$/Hal/Cp composite at low magnification, and FIG. 5D is $CeO_2$/Hal/Cp composite at high magnification.

FIGS. 11A-11N show light microscopy images HFF-1 cells which were untreated (FIGS. 11A-11B) and treated with various nanocomposite groups for 48 h as follows: 200 µg/mL of $CeO_2$/Silica/Cp/Cur (FIG. 11C), 400 µg/mL of $CeO_2$/Silica/Cp/Cur (FIG. 11D), 200 µg/mL of $CeO_2$/Hal/Cur (FIG. 11E), 400 µg/mL of $CeO_2$/Hal/Cur (FIG. 11F), 200 µg/mL of $CeO_2$/Silica (FIG. 11G), 400 µg/mL of $CeO_2$/Silica (FIG. 11H), 200 µg/mL of $CeO_2$/Hal (FIG. 11I), 400 µg/mL of $CeO_2$/Hal (FIG. 11J), 200 µg/mL of curcumin (FIG. 11K), 400 µg/mL of curcumin (FIG. 11L), 200 µg/mL of cisplatin (FIG. 11M), and 400 µg/mL of cisplatin (FIG. 11N).

DETAILED DESCRIPTION OF THE INVENTION

Figure 1:
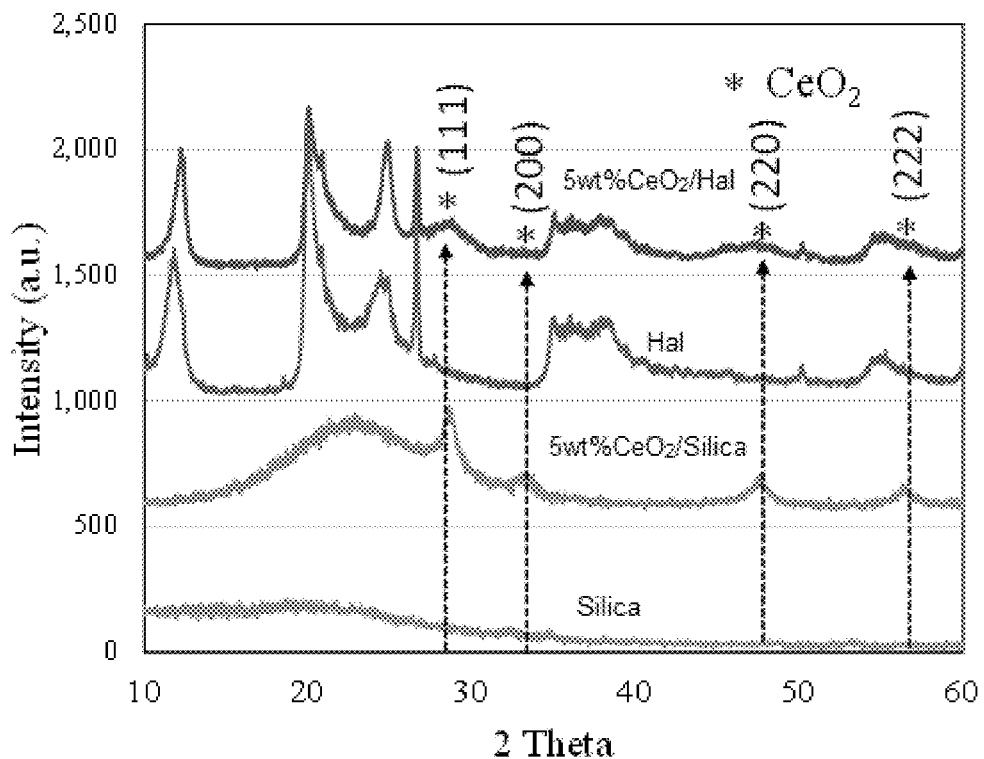
FIG. 1 shows X-ray diffraction patterns of Silica, 5 wt % $CeO_2$/Silica, Hal, and 5 wt % $CeO_2$/Hal.

In the following description, it is understood that other embodiments may be utilized and structural and operational changes may be made without departure from the scope of the present embodiments disclosed herein.

Definitions

As used herein the words "a" and "an" and the like carry the meaning of "one or more."

As used herein, the terms "optional" or "optionally" mean that the subsequently described event(s) can or cannot occur or the subsequently described component(s) may or may not be present (e.g., 0 wt. %).

According to a first aspect, the present disclosure relates to a nanomedicinal composition comprising a nanocarrier and a pharmaceutical agent mixture comprising a platinum (II) complex and an antioxidant. The nanocarrier comprises a porous silicate and/or aluminosilicate matrix and cerium oxide nanoparticles disposed in the pores of the porous silicate and/or aluminosilicate matrix. The pharmaceutical agent mixture is disposed in the pores of and/or on a surface of the nanocarrier.

In general, any suitable silicate and/or aluminosilicate matrix known to one of ordinary skill in the art may be used in the nanomedicinal composition. Examples of such suitable porous silica, silicate, or aluminosilicate materials include, but are not limited to, MCM-41, MCM-48, Q-10 silica, hydrophobic silica, mesobeta, mesoZSM-5, SBA-15, KIT-5, KIT-6, mesosilicalite, hierarchical porous silicalite, SBA-16, mesoporous silica spheres, and halloysite. The term "silicate matrix" should be understood to include silica itself. Methods of obtaining the various types porous silica, silicate, or aluminosilicate material are well-known in the art [see for example Gobin, Oliver Christian "SBA-16 Materials: Synthesis, Diffusion, and Sorption Properties" Dissertation, Laval University, Ste-Foy, Quebec, Canada, January 2006, in particular section 2.2; and U.S. patent application Ser. No. 15/478,794—both incorporated herein by reference in their entireties]. In some embodiments, the porous silicate and/or aluminosilicate matrix is a combination of mesoporous silica spheres and halloysite. In some embodiments, the halloysite is present as nanotubes. Such nanotubes may be referred to as "halloysite nanotubes".

Aluminosilicate materials may be characterized by a ratio of Si to Al present in the material. In general, the aluminosilicate material may have any suitable Si:Al molar ratio. Examples of such suitable Si:Al molar ratios are 1000:1 to 1:250, preferably 500:1 to 1:200, preferably 250:1 to 1:100, preferably 150:1 to 1:75, preferably 100:1 to 1:50, preferably 50:1 to 1:25, preferably 25:1 to 1:10, preferably 10:1 to 1:5, preferably 5:1 to 1:2.5, preferably 2.5:1 to 1:1.5, preferably 1.5:1 to 1:1. In general, the elemental composition of the silicate and/or aluminosilicate material, including the Si:Al molar ratio, may be determined by any suitable technique known to one of ordinary skill in the art. Examples of suitable such techniques include mass spectrometry techniques such as inductively-coupled plasma mass spectrometry (ICP-MS), atomic emission spectroscopy techniques such as inductively-coupled plasma atomic emission spectroscopy (ICP-AES) (also referred to as ICP optical emission spectroscopy, ICP-OES), atomic absorption spectroscopy techniques such as inductively-coupled plasma atomic absorption spectroscopy (ICP-AAS), and X-ray spectroscopy techniques such as X-ray photoelectron spectroscopy.

Silicates and aluminosilicates are materials which comprise $SiO_4$ tetrahedra (and $AlO_4^-$ tetrahedra, $AlO_6$ octahedra, and/or $Al(OH)_6$ octahedra in the case of aluminosilicates) joined together in a wide variety of structural motifs. The tetrahedra (and if applicable octahedra) in the silicate and/or aluminosilicate material of the present invention may in general adopt any structural motif present in other silicate materials, such as isolated tetradhedra as in neosilicates (single tetrahedra, also called orthosilicates) and sorosilicates (double tetrahedra), chains of tetrahedra such as inosilicates (both single chain as in pyroxene group silicates and double chain as in amphibole group silicates), rings of tetrahedra as in cyclosilicates, sheets of tetrahedra as in phyllosilicates, and three-dimensional frameworks as in tectosilicates. In some aluminosilicates, the material comprises a substructure comprising silicon-containing and/or aluminum-containing tetrahedral and a substructure comprising aluminum-containing octahedral. An example of such an arrangement is the mineral kaolin, which comprises sheets of alternating tetrahedra-containing layers and octahedra-containing layers. The arrangement of isolated tetrahedra, chains of tetrahedra, sheets of tetrahedra, or three-dimensional frameworks may give rise to channels, pores, cages, or other spaces within the silicate and/or aluminosilicate which is capable of hosting material which is not the silicate and/or aluminosilicate itself. Examples of materials, particularly those relevant to the current disclosure, include water, organic molecules, and inorganic nanoparticles. While the larger structures formed of tetrahedra (i.e. chains, rings, sheets, and three-dimensional frameworks) may themselves be ordered, the arrangement of these larger structures may be disordered. Such disorder may give rise to a material which is amorphous by techniques for determining crystallinity or crystal structure such as powder X-ray diffraction (PXRD). Alternatively, the larger structures may be ordered, giving rise to a crystalline material.

Halloysite is a naturally occurring clay material comprising nanotubes made of aluminosilicate kaolin sheets rolled into a tube shape. Sometimes the kaolin sheets are rolled several times. As described above, such kaolin sheets comprise a tetrahedral layer comprising silicon-containing tetrahedra and an octahedral layer comprising aluminum-containing octahedral. These sheets are typically rolled to place the tetrahedral layer on the exterior surface of the nanotube and the octahedral layer on the interior surface of the nanotube. The silicon-rich tetrahedral layer gives the halloysite nanotube an exterior surface rich in siloxane functional groups and typically a negative charge. The aluminum-rich octahedral layer gives the halloysite nanotube an interior surface rich in aluminol functional groups and typically a positive charge. The size and shape of halloysite nanotubes are typically defined by a nanotube outer diameter, a nanotube length, and sometimes an aspect ratio. Sometimes an inner diameter or a nanotube wall thickness is also used to further define the size and shape of nanotubes. In some embodiments, the halloysite nanotubes have a mean nanotube outer diameter of 10 to 125 nm, preferably 12.5 to 110 nm, preferably 15 to 100 nm, preferably 17.5 to 95 nm, preferably 20 to 90 nm, preferably 22.5 to 85 nm, preferably 25 to 80 nm, preferably 27.5 to 75 nm, preferably 30 to 70 nm. In some embodiments, the halloysite nanotubes have a mean inner diameter of 5 to 22.5 nm, preferably 7.5 to 20 nm, preferably 10 to 17.5 nm, preferably 11 to 16 nm, preferably 12 to 15 nm. In some embodiments, the halloysite nanotubes have a mean nanotube length of 0.25 to 7.5 µm, preferably 0.35 to 7 µm, preferably 0.5 to 5 µm preferably 0.75 to 4 µm, preferably 0.9 to 3.5 µm, preferably 1 to 3 µm. In some embodiments, the halloysite nanotubes have an aspect ratio of 2:1 to 750:1, preferably 5:1 to 500:1, preferably 7.5:1 to 250:1, preferably 10:1 to 150:1, preferably 12.5:1 to 125:1, preferably 14:1 to 100:1.

The shape of the halloysite nanotubes, being hollow, gives the halloysite nanotubes an interior surface and an exterior surface. In some embodiments, the interior surface is substantially the same as the exterior surface. In this context, "substantially the same" may refer to or be measured by any suitable structural or functional parameter or property known to one of ordinary skill in the art. Examples of such suitable structural parameters or properties include, but are not limited to chemical composition (including in particular Si:Al molar ratio), charge identity or density, orientation of tetrahedra, porosity, crystallographic characteristic such as strain or orientation, functional group identity or density, and binding or adsorption affinity for organic molecules and/or inorganic materials. In alternative embodiments, the interior surface is not substantially the same as the exterior surface. In some embodiments, the halloysite nanotubes have an exterior surface which is negatively charged and an interior surface which is positively charged. In some embodiments, such a charge difference is the result of a compositional difference between the exterior surface and the interior surface. Such a compositional difference may be in the form of a difference in an amount of silicon and/or aluminum present. In some embodiments, the exterior surface is silicon-rich (e.g. having a Si:Al molar ratio of approximately 1000:1 to 5:1). In some embodiments, the interior surface is aluminum-rich (e.g. having a Si:Al molar ratio of 1:2.5 to 1:250).

The shape of the halloysite nanotubes encloses an interior volume bound by the interior surface of the nanotube. The interior volume may be substantially cylindrical in shape. The halloysite nanotubes have at least one (preferably both) ends open, permitting substances to pass into the interior volume through said open ends. Materials (e.g. the cerium oxide nanoparticles and/or pharmaceutical agent mixture) may be contained within the interior volume. Such materials may remain within the interior volume though interaction with the interior surface of the halloysite nanotube. In some embodiments, the layers of the silicate and/or aluminosilicate material may further comprise in-layer pores. Such in-layer pores are preferably oriented substantially perpendicular to the length of the nanotube. The in-layers pores may allow access to the interior volume or to an interlayer volume described below. Such pores may comprise a pore wall. This pore wall is a distinct surface from the interior surface and the exterior surface of the halloysite nanotube. The pore wall may be substantially the same as one or both of the interior surface and the exterior surface of the halloysite nanotube. Alternatively, the pore wall may be distinct from the interior surface or the exterior surface in terms of properties such as chemical composition (including in particular Si:Al molar ratio), charge identity or density, orientation of tetrahedra, crystallographic characteristic such as strain or orientation, functional group identity or density, and binding or adsorption affinity for organic molecules and/or inorganic materials. Embodiments in which the halloysite nanotubes comprise more than one layer of silicate and/or aluminosilicate material, the nanotubes may further comprise an interlayer volume defined between the layers. The interlayer volume may be defined by an inner interlayer surface and an outer interlayer surface. Due to the orientation, the inner interlayer surface may be substantially the same as the exterior surface of the halloysite nanotube while the outer interlayer surface may be substantially the same as the interiors surface of the nanotube. The interlayer volume may be accessible at the open ends of the halloysite nanotubes or by in-layer pores described above.

In some embodiments, the porous silicate and/or aluminosilicate matrix is surface modified prior to use in the nanocarrier. Such surface modifications may change the surface properties of the porous silicate and/or aluminosilicate matrix, for example by increasing or decreasing the number or concentration of functional groups found on an unmodified porous silicate and/or aluminosilicate matrix or by introducing new functional groups to the porous silicate and/or aluminosilicate matrix. Examples of such new functional groups include, but are not limited to carboxylic acid or carboxylate groups, amine or ammonium groups, sulfo groups, and phosphate groups. Such functional groups may be charged or uncharged. In some embodiments, the surface modification changes the surface charge of the interior surface, the exterior surface, the pore surface, or any combination thereof of the modified porous silicate and/or aluminosilicate matrix compared to unmodified porous silicate and/or aluminosilicate matrix. Preferably, the surface modification does not change the surface charge of the interior surface, exterior surface, pore surface, or any combination thereof of the modified porous silicate and/or aluminosilicate matrix compared to unmodified porous silicate and/or aluminosilicate matrix. Such surface modification may be performed using any suitable method or with any suitable surface modifying agent or agents known to one of ordinary skill in the art. One example of such a method is the use of silanes or organosilicates bearing one or more functional groups to be added by the surface modification. Such surface modification may result in said functional groups being attached to the porous silicate and/or aluminosilicate matrix by covalent bonds. Alternatively, said functional groups may be attached to the porous silicate and/or aluminosilicate matrix by a non-covalent interaction, for example electrostatic interaction, physisorption, or hydrogen bonding. For an example of such surface modification particularly relevant to embodiments of the current invention which use halloysite nanotubes, see U.S. published application US20190270646A1. In some embodiments, the surface modifying agent(s) are substantially free of silanes. In some embodiments, the surface modifying agent(s) are substantially free of organosilicates. In some embodiments, the surface modifying agent(s) are substantially free of amino acids. In some embodiments, the surface modifying agent(s) are substantially free of short peptides (i.e. 2-20 residues). In some embodiments, the surface modifying agent(s) are substantially free of chromium salts (chrome alum, chromium acetate, etc.); calcium salts (calcium chloride, calcium hydroxide, etc.); aluminum salts (aluminum chloride, aluminumhydroxide, etc.); dialdehydes (glutaraldehyde, etc.); carbodiimides (EDC, WSC, N-hydroxy-5-norbomene-2,3-di-carboxylmide (HONB), N-hydroxysuccinic acid imide (HOSu), dicyclohexylcarbodiimide (DCC), etc.); N-hydrox-ysuccinimide; and/or phosphorus oxychloride. In some embodiments, the surface modifying agent(s) are substantially free of proteins. Examples of such proteins include, but are not limited to collagen, gelatin, albumin, ovalbumin, casein, transferrin, fibrin, and fibrinogen.

In an embodiment, the porous silicate and/or aluminosilicate matrix is in the form of particles of mesoporous silica which are substantially spherical and have a mean particle size of 50 to 110 nm, preferably 55 to 105 nm, preferably 60 to 100 nm, preferably 65 to 95 nm preferably 70 to 90 nm, preferably 75 to 85 nm, preferably 80 nm. In an embodiment, the particles of mesoporous silica which are amorphous by Powder X-ray Diffraction (PXRD).

In some embodiments, the porous silicate and/or aluminosilicate matrix is present in an amount of 55 to 85 wt %, preferably 57.5 to 82.5 wt %, preferably 60 to 80 wt %, preferably 62.5 to 77.5 wt %, preferably 65 to 75 wt %, preferably 67.5 to 72.5 wt %, preferably 69 to 71 wt %, preferably 70 wt %, based on a total weight of the nanocarrier.

In some embodiments, the nanocarrier has a surface area of 15 $m^2$/g to 100 $m^2$/g, preferably 20 $m^2$/g to 95 $m^2$/g, preferably 25 $m^2$/g to 80 $m^2$/g, preferably 30 $m^2$/g to 75 $m^2$/g.

In some embodiments, the porous silicate and/or aluminosilicate matrix is particles of mesoporous silica and the nanocarrier has a surface area of 15 to 45 $m^2$/g, preferably 17.5 to 42.5 $m^2$/g, preferably 20 to 40 $m^2$/g, preferably 22.5 to 37.5 $m^2$/g, preferably 25 to 35 $m^2$/g, preferably 27.5 to 32.5 $m^2$/g, preferably 29 to 31 $m^2$/g, preferably 30 $m^2$/g. In some embodiments, the porous silicate and/or aluminosilicate matrix is halloysite nanotubes and the nanocarrier has a surface area of 40 to 100 $m^2$/g, preferably 45 to 90 $m^2$/g, preferably 50 to 85 $m^2$/g, preferably 55 to 80 $m^2$/g, preferably 57.5 to 75 $m^2$/g, preferably 60 to 72.5 $m^2$/g, preferably 62.5 to 70 $m^2$/g, preferably 65 to 67.5 $m^2$/g.

In some embodiments, the nanocarrier has a mean pore size of 1 nm to 60 nm, preferably 2.5 to 50 nm, preferably 5 nm to 40 nm, preferably 7.5 nm to 35 nm, preferably 10 nm to 30 nm. In some embodiments, the porous silicate and/or aluminosilicate matrix is particles of mesoporous silica and the nanocarrier has a mean pore size of 14 to 30 nm, preferably 15 to 28 nm, preferably 16 to 27 nm, preferably 17 to 26 nm, preferably 18 to 25 nm, preferably 19 to 24 nm, preferably 20 to 23 nm, preferably 21 to 22 nm. In some embodiments, the porous silicate and/or aluminosilicate matrix is halloysite nanotubes and the nanocarrier has a mean pore size of 10 to 22 nm, preferably 11 to 21 nm, preferably 12 to nm, preferably 13 to 19 nm, preferably 14 to 18 nm, preferably 15 to 17 nm, preferably 16 nm. In some embodiments, the porous silicate and/or aluminosilicate matrix comprises a first set of pores having a mean pore size of 14 to 30 nm, preferably 15 to 28 nm, preferably 16 to 27 nm, preferably 17 to 26 nm, preferably 18 to 25 nm, preferably 19 to 24 nm, preferably 20 to 23 nm, preferably 21 to 22 nm and a second set of pores having a mean pore size of 10 to 22 nm, preferably 11 to 21 nm, preferably 12 to 20 nm, preferably 13 to 19 nm, preferably 14 to 18 nm, preferably 15 to 17 nm, preferably 16 nm.

In some embodiments, the nanocarrier has a mean pore volume of 0.05 to 0.37 $cm^3$/g, preferably 0.1 to 0.325 $cm^3$/g, preferably 0.125 to 0.30 $cm^3$/g, preferably 0.15 to 0.275 $cm^3$/g. In some embodiments, the porous inorganic matrix is particles of mesoporous silica and the nanocarrier has a mean pore volume of 0.05 to 0.25 cm$^3$/g, preferably 0.1 to 0.225 cm$^3$/g, preferably 0.11 to 0.21 cm$^3$/g, preferably 0.12 to 0.20 cm$^3$/g, preferably 0.13 to 0.19 cm$^3$/g, preferably 0.14 to 0.18 cm$^3$/g, preferably 0.15 to 0.17 cm$^3$/g, preferably 0.16 cm$^3$/g. In some embodiments, the porous inorganic matrix is halloysite nanotubes and the nanocarrier has a mean pore volume of 0.15 to 0.37 cm$^3$/g, 0.16 to 0.36 cm$^3$/g, preferably 0.17 to 0.35 cm$^3$/g, preferably 0.18 to 0.34 cm$^3$/g, preferably 0.19 to 0.33 cm$^3$/g, preferably 0.20 to 0.32 cm$^3$/g, preferably 0.21 to 0.31 cm$^3$/g, preferably 0.22 to 0.30 cm$^3$/g, preferably 0.23 to 0.29 cm$^3$/g, preferably 0.24 to 0.28 cm$^3$/g, preferably 0.25 to 0.27 cm$^3$/g, preferably 0.26 cm$^3$/g. In some embodiments, the porous silicate and/or aluminosilicate matrix comprises a first set of pores having a mean pore volume of 0.05 to 0.25 cm$^3$/g, preferably 0.1 to 0.225 cm$^3$/g, preferably 0.11 to 0.21 cm$^3$/g, preferably 0.12 to 0.20 cm$^3$/g, preferably 0.13 to 0.19 cm$^3$/g, preferably 0.14 to 0.18 cm$^3$/g, preferably 0.15 to 0.17 cm$^3$/g, preferably 0.16 cm$^3$/g and a second set of pores having a mean pore volume of 0.15 to 0.37 cm$^3$/g, 0.16 to 0.36 cm$^3$/g, preferably 0.17 to 0.35 cm$^3$/g, preferably 0.18 to 0.34 cm$^3$/g, preferably 0.19 to 0.33 cm$^3$/g, preferably 0.20 to 0.32 cm$^3$/g, preferably 0.21 to 0.31 cm$^3$/g, preferably 0.22 to 0.30 cm$^3$/g, preferably 0.23 to 0.29 cm$^3$/g, preferably 0.24 to 0.28 cm$^3$/g, preferably 0.25 to 0.27 cm$^3$/g, preferably 0.26 cm$^3$/g.

In some embodiments, the porous silicate and/or aluminosilicate matrix is present in the form of particles. In general, the porous silicate and/or aluminosilicate matrix particles can be any shape known to one of ordinary skill in the art. Examples of suitable shapes the porous silicate and/or aluminosilicate matrix particles may take include spheres, spheroids, lentoids, ovoids, solid polyhedra such as tetrahedra, cubes, octahedra, icosahedra, dodecahedra, rectangular prisms, triangular prisms (also known as nanotriangles), nanoplatelets, nanodisks, blocks, flakes, discs, granules, angular chunks, and mixtures thereof. Nanorods or nanowires are not a shape that the porous silicate and/or aluminosilicate matrix particles are envisioned as having in any embodiments.

In some embodiments, the porous silicate and/or aluminosilicate matrix particles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of porous silicate and/or aluminosilicate matrix particles having a different shape. As used herein, the term "non-uniform shape" refers to an average consistent shape that differs by more than 10% of the distribution of porous silicate and/or aluminosilicate matrix particles having a different shape. In one embodiment, the shape is uniform and at least 90% of the porous silicate and/or aluminosilicate matrix particles are spherical or substantially circular, and less than 10% are polygonal. In another embodiment, the shape is non-uniform and less than 90% of the porous silicate and/or aluminosilicate matrix particles are spherical or substantially circular, and greater than 10% are polygonal.

In some embodiment, the porous silicate and/or aluminosilicate matrix is in the form of particles having a mean particle size of 50 to 110 nm, preferably 55 to 105 nm, preferably 60 to 100 nm, preferably 65 to 95 nm preferably 70 to 90 nm, preferably 75 to 85 nm, preferably 80 nm. In embodiments where the porous silicate and/or aluminosilicate matrix particles are spherical, the particle size may refer to a particle diameter. In embodiments where the porous silicate and/or aluminosilicate matrix particles are polyhedral, the particle size may refer to the diameter of a circumsphere. In some embodiments, the particle size refers to a mean distance from a particle surface to particle centroid or center of mass. In alternative embodiments, the particle size refers to a maximum distance from a particle surface to a particle centroid or center of mass. In some embodiments where the porous silicate and/or aluminosilicate matrix particles have an anisotropic shape such as nanorods or nanotubes, the particle size may refer to a length of the nanorod or nanotube, a width of the nanorod or nanotube, or an average of the length and width of the nanorod or nanotube. In some embodiments, the particle size refers to the diameter of a sphere having an equivalent volume as the particle.

In some embodiments, the porous silicate and/or aluminosilicate matrix particles are in the form of nanotubes having a mean size as described above for halloysite nanotubes.

In some embodiments, the porous silicate and/or aluminosilicate matrix particles are monodisperse, having a coefficient of variation or relative standard deviation, expressed as a percentage and defined as the ratio of the particle size standard deviation ($\sigma$) to the particle size mean ($\mu$) multiplied by 100 of less than 25%, preferably less than 10%, preferably less than 8%, preferably less than 6%, preferably less than 5%, preferably less than 4%, preferably less than 3%, preferably less than 2%. In some embodiments, the porous silicate and/or aluminosilicate matrix particles of the present disclosure are monodisperse having a particle size distribution ranging from 80% of the average particle size to 120% of the average particle size, preferably 90-110%, preferably 95-105% of the average particle size. In some embodiments, the porous silicate and/or aluminosilicate matrix particles are not monodisperse.

In some embodiments, the porous silicate and/or aluminosilicate matrix particles comprise first particles having a mean particle size of 50 to 110 nm, preferably 55 to 105 nm, preferably 60 to 100 nm, preferably 65 to 95 nm preferably 70 to 90 nm, preferably 75 to 85 nm, preferably 80 nm and second particles which are nanotubes having have a mean nanotube outer diameter of 10 to 125 nm, preferably 12.5 to 110 nm, preferably 15 to 100 nm, preferably 17.5 to 95 nm, preferably 20 to 90 nm, preferably 22.5 to 85 nm, preferably to 80 nm, preferably 27.5 to 75 nm, preferably 30 to 70 nm, a mean inner diameter of 5 to 22.5 nm, preferably 7.5 to 20 nm, preferably 10 to 17.5 nm, preferably 11 to 16 nm, preferably 12 to 15 nm, and a mean nanotube length of 0.25 to 7.5 µm, preferably 0.35 to 7 µm, preferably 0.5 to 5 µm preferably 0.75 to 4 µm, preferably 0.9 to 3.5 µm, preferably 1 to 3 µm. In some such embodiments, the first particles are spherical as described above.

The nanocarrier also comprises cerium oxide nanoparticles. In some embodiments, the cerium oxide nanoparticles are present in an amount of 1 to 10 wt %, preferably 1.5 to 9.5 wt %, preferably 2 to 8 wt %, preferably 2.5 to 7.5 wt %, preferably 3 to 7 wt %, preferably 3.5 to 6.5 wt %, preferably 4 to 6 wt %, preferably 4.25 to 5.75 wt %, preferably 4.5 to 5.5 wt %, preferably 4.75 to 5.25 wt %, preferably 5 wt %, based on a total weight of the nanocarrier.

In general, the cerium oxide nanoparticles can be any shape known to one of ordinary skill in the art as described above. In some embodiments, the cerium oxide nanoparticles have a mean particle size of 1 to 20 nm, preferably 2.5 to 17.5 nm, preferably 5 to 15 nm, preferably 7.5 to 12.5 nm, preferably 8 to 12 nm, preferably 9 to 11 nm, preferably 10 nm. In some embodiments, the cerium oxide nanoparticles are monodisperse as described above. In some embodiments, the cerium oxide nanoparticles are not monodisperse.

The incorporation of the cerium oxide nanoparticles occupies a portion of the pores present in the porous silicate and/or aluminosilicate matrix. In some embodiments, the incorporation of the cerium oxide nanoparticles reduces a post-nanoparticle incorporation pore volume of the porous silicate and/or aluminosilicate matrix to 30 to 95%, preferably 35 to 90%, preferably 40 to 85%, preferably 45 to 80%, preferably 50 to 77.5% of an initial pore volume of the porous silicate and/or aluminosilicate matrix. That is, the nanocarrier has a pore volume of 30 to 95%, preferably 35 to 90%, preferably 40 to 85%, preferably 45 to 80%, preferably 50 to 77.5% of the pore volume of the porous silicate and/or aluminosilicate matrix.

In general, the platinum (II) complex may be any suitable platinum (II) complex known to one of ordinary skill in the art. In preferred embodiments, the platinum (II) complex is any platinum (II) complexes effective for treatment of cancer. Examples of such platinum (II) complexes include, but are not limited to, cisplatin, carboplatin, oxaliplatin, nedaplatin, triplatin tetranitrate, phenanthriplatin, picoplatin, strataplatin or mixtures thereof.

In some embodiments, the platinum (II) complex is at least one selected from the group consisting of cisplatin, carboplatin, and oxaliplatin. In preferred embodiments, the platinum (II) complex is cisplatin.

In general, the antioxidant may be any suitable antioxidant known to one of ordinary skill in the art. Examples of such antioxidants include, but are not limited to curcumin (and curcumin derivatives known as curcuminoids), Coenzyme Q10, quercetin, rutin, ascorbic acid, gallic acid, edaravone, N-acetylcysteine, alfa-lipoic acid, diosmin, hesperidin, oxerutins, baicalein, tocotrienols, resveratrol or other stilbenoids such as pterostilbene, retinoids and carotenes including Vitamin A, beta carotene, and alpha-carotene, astaxanthin, canthaxanthin, lutein, lycopene, and zeaxanthin, natural phenols including flavonoids, silymarin, xanthones, eugenol, phenolic acids, lipoic acid, acetylcysteine, uric acid, glutathione, and catechin. In some embodiments, the antioxidant is at least one selected from the group consisting of quercetin, rutin, coenzyme Q10, gallic acid, and curcumin.

Quercetin has the following chemical structure:

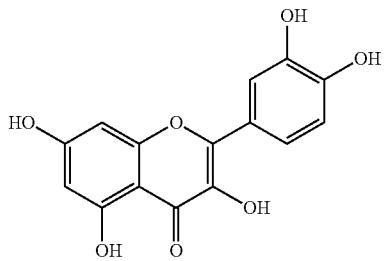 [SMILES: O=c1c(O)c(-c2ccc(O)c(O)c2)oc2cc(O)cc(O)c12]

Quercetin is a plant flavonol from the flavonoid group. It is found in a wide variety of food sources, but has very low water solubility and bioavailability. Inclusion of quercetin in the nanomedicinal composition of the present invention may overcome these disadvantageous properties of quercetin to increase an amount of quercetin which is delivered. Quercetin may be present in a crystalline or amorphous form or in a mixture of both crystalline and amorphous forms, for example at a ratio of 1-99 wt. %:99-1 wt. %, 10-90 wt. %:90-10 wt. %; 20-80 wt. %:80-20 wt. %, 30-70 wt. %:70-30 wt. %, 40-60 wt. %:60-40 wt. % or about 50 wt. %:about 50 wt. % (or any intermediate ratio of crystalline:amorphous forms).

Rutin has the following structure:

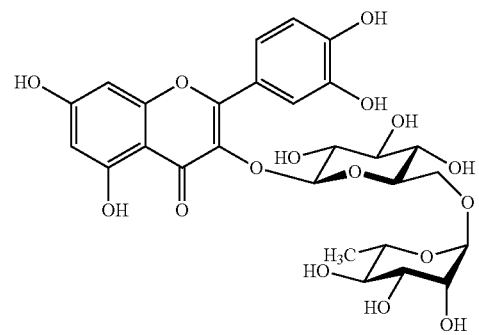

Rutin is the glycoside combining the flavonol quercetin and the disaccharide rutinose (α-L-rhamnopyranosyl-(1→6)-β-D-glucopyranose). Rutin may be present in a crystalline or amorphous form or in a mixture of both crystalline and amorphous forms, for example at a ratio of 1-99 wt. %:99-1 wt. %, 10-90 wt. %:90-10 wt. %; 20-80 wt. %:80-20 wt. %, 30-70 wt. %:70-30 wt. %, 40-60 wt. %:60-40 wt. % or about 50 wt. %:about 50 wt. % (or any intermediate ratio of crystalline:amorphous forms).

Coenzyme Q10 (CoQ10) conforms to the following chemical structure:

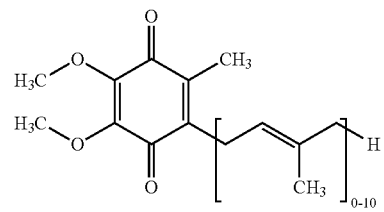

CoQ10 is a 1,4-benzoquinone, where Q refers to the quinone chemical group and 10 refers to the number of isoprenyl chemical subunits in its tail. Other forms of Coenzyme Q may be distinguished from CoQ10 by their number of isoprenyl subunits. A CoQ such as CoQ10 may be present in a crystalline or amorphous form or in a mixture of both crystalline and amorphous forms, for example at a ratio of 1-99 wt. %:99-1 wt. %, 10-90 wt. %:90-10 wt. %; 20-80 wt. %:80-20 wt. %, 30-70 wt. %:70-30 wt. %, 40-60 wt. %:60-40 wt. % or about 50 wt. %:about 50 wt. % (or any intermediate ratio of crystalline:amorphous forms).

Gallic acid has the following structure:

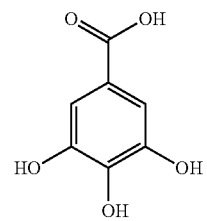

Gallic acid is a potent antioxidant against cancers (leukemia, colon and lung cancer cells) and other metabolic disorders. Gallic acid may be present in a crystalline or amorphous form or in a mixture of both crystalline and amorphous forms, for example at a ratio of 1-99 wt. %:99-1 wt. %, 10-90 wt. %:90-10 wt. %; 20-80 wt. %:80-20 wt. %, 30-70 wt. %:70-30 wt. %, 40-60 wt. %:60-40 wt. % or about 50 wt. %:about 50 wt. % (or any intermediate ratio of crystalline:amorphous forms).

Curcumin has the following structure:

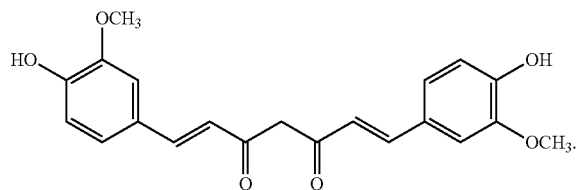 [SMILES: COc1cc(/C=C/C(=O)CC(=O)/C=C/c2ccc(O)c(OC)c2)ccc1O]

A curcuminoid is a linear diarylheptanoid. This class of compounds includes curcumin in both its keto and enolate forms as well as curcumin derivatives such as demethoxycurcumin and bisdemethoxycurcumin and their geometrical isomers and metabolites including sulfate conjugates and glucoronides. Other examples of curcumin derivatives or analogs include those described by Raja, et al., U.S. Pat. No. 9,447,023 B2, Raja, et al., U.S. Pat. No. 9,650,404 B2, Johnson, et al., U.S. Pat. No. 9,556,105 B2 or Vander Jagt, et al., U.S. Pat. No. 9,187,397 B2 (all incorporated by reference); especially for their descriptions of curcuminoid formulas and various chemical species of curcuminoids. In some embodiments of the invention curcumin or another curcuminoid may be included as an antioxidant in the nanomedicinal composition of the present disclosure.

Mixtures of curcuminoids are also contemplated such as one isolated from rhizomes of turmeric comprised of Curcumin (75-81%), Demethoxycurcumin (15-19%) and Bisdemethoxycurcumin (2.5-6.5%). The content of any one of a curcuminoid in a mixture may range from about 0 to about 100 wt. %, for example, 10-90 wt. %, 20-80 wt. %, 30-70 wt. %, 40-60 wt %., 50 wt. %, 40 wt. %, 33.3 wt. %, 30 wt. %, 20 wt. %, 10 wt. % or 5 wt % or 1 wt. %. A mixture may contain two, three or more different curcuminoids.

Curcumin may be present in a crystalline or amorphous form or in a mixture of both crystalline and amorphous forms, for example at a ratio of 1-99 wt. %:99-1 wt. %, 10-90 wt. %:90-10 wt. %; 20-80 wt. %:80-20 wt. %, 30-70 wt. %:70-30 wt. %, 40-60 wt. %:60-40 wt. % or about 50 wt. %:about 50 wt. % (or any intermediate ratio of crystalline:amorphous forms). In some embodiments disclosed herein, curcumin will be in an amorphous form to increase its solubility.

Curcumin and its derivatives are known for their antimicrobial, anti-oxidative, anti-inflammatory, and anti-cancer properties such as malignancies in the brain or nervous system. Curcumin has also been proposed as an agent to treat oxidative stress, such as oxidative stress in the brain, and for treatment of neurodegenerative disease like Alzheimer's disease ("AD") or Parkinson's disease ("PD"); Lee, et al., Curr. Neuropharmacol. 2013 July; 11(4):338-378 (incorporated by reference).

Curcumin may also be functionalized or prepared as a conjugate with another moiety to modify or improve its pharmacokinetic properties. For example, curcumin can be adsorbed through functionalization to a silane, carboxylic acid, or biotin. Biocompatibility of a curcuminoid/hierarchical aluminosilicate can be increased by the modification with chitosan, or poly (D,L-lactide-co-glycolide), or polyethylene glycol.

In preferred embodiments, the antioxidant is curcumin.

In some embodiments, a weight ratio of the antioxidant to the anti-cancer therapeutic is 1:1 to 10:1, preferably 2:1 to 9:1, preferably 3:1 to 8:1, preferably 4:1 to 7:1, preferably 5:1 to 6:1.

In some embodiments, the pharmaceutical agent mixture is present in the nanomedicinal composition in an amount of 5 to 50 wt %, preferably 10 to 47.5 wt %, preferably 15 to 45 wt %, preferably 17.5 to 42.5 wt %, preferably 20 to 40 wt %, preferably 22.5 to 37.5 wt %, preferably 25 to 35 wt %, preferably 26 to 34 wt %, preferably 27 to 33 wt %, preferably 28 to 31 wt %, preferably 29 to 30 wt %, based on a total weight of nanomedicinal composition.

In some embodiments, the pharmaceutical agent mixture or its constituent compounds may interact with the surface of the nanocarrier via any suitable interaction known to one of ordinary skill in the art. Such interactions may be, for example physisorption (e.g. Van der Waals interactions), ion-ion interactions, ion-dipole interactions, dipole-dipole interactions, and hydrogen bonding. Such interaction may be through or involving appropriate functional groups on the platinum (II) complex and/or the antioxidant. Examples of such functional groups include, but are not limited to oxygen-containing functional groups such as alcohols, alkoxides, carboxylic acids and carboxylates, esters, ketones, and ethers; nitrogen-containing functional groups such as amines, amides, azides, diimides, imines, porphyrins, imides, isonitriles, nitriles, and nitro functional groups; phosphorous-containing functional groups such as phosphines, phosphites, phosphates, phosphonites, phosphonates, phosphinites, and phosphinates; and sulfur-containing functional groups such as thiols, thiolates, disulfides, sulfones, sulfonic acids and sulfonates, sulfoxides, thials, thioesters, thiosulfinates, thiocarboxylic acids and thiocarboxylates, sulfinic acids and sulfinates, thiocyanates, and isothiocyanates. The platinum (II) complex and/or the antioxidant may be electrically neutral or may have a charge, the charge being either positive or negative. A compound which is electrically neural may be devoid of charges or may have a combination of positive and negative charges in equal number so as to balance to electrically neutral (e.g. zwitterionic). A compound which is electrically neutral may interact to an equal extent with or be disposed equally upon both the interior and exterior surfaces of the nanocarrier. Alternatively, a compound which is electrically neutral may preferentially interact with either the interior or exterior surface of the nanocarrier. A compound which bears a positive charge may preferentially interact with or be disposed upon the exterior surface of the nanocarrier which bears a negative charge. A compound which bears a negative charge may preferentially interact with or be disposed upon the interior surface of the nanocarrier which bears a positive charge.

In some embodiments, the nanomedicinal composition comprises a biocompatible coating. Such a biocompatible coating may be disposed upon the nanocarrier and/or the pharmaceutical agent mixture. In general, the biocompatible coating may be any suitable coating known to one of ordinary skill in the art. Examples of such suitable biocompatible coatings include, but are not limited to, agarose, agar, carrageen, alginic acid, alginate, an alginic acid derivative, a hyaluronate derivative, a polyanionic polysaccharide, chitin, chitosan, fibrin, a polyglycolide, a polylactide, a polycaprolactone, a dextran or copolymer thereof, polyvinyl pyrrolidone, a polyacrylate, a wax, a polyethylene-polyoxypropylene-block polymer, wool fat, poly(L-lactic acid), poly(DL-Lactic acid) copoly(lactic/glycolic acid), cellulose, a cellulose derivative, a glycol, polylactide-polyglycolide, polymethyldisiloxane, polycaprolactone, polylactic acid, and ethylene vinyl acetate.

In some embodiments, the nanomedicinal composition releases greater than 15%, preferably greater than 15.5%, preferably greater than 16%, preferably greater than 16.5%, preferably greater than 17%, preferably greater than 17.5%, preferably greater than 18%, preferably greater than 18.5%, preferably greater than 19%, preferably greater than 19.5%, preferably greater than 20% of a total weight of platinum (II) complex within 6 to 12 hours, preferably 7 to 11 hours, preferably 8 to 10 hours of contact with a suitable biological medium. Examples of suitable biological media include, but are not limited to, buffered saline solutions such as phosphate buffered saline, cell culture media such as Minimum Essential Medium (MEM, also known as Eagle's minimal essential medium EMEM), Dulbecco's Modified Eagle's Medium (DMEM), Iscove's Modified Dulbecco's Medium (IMDM), RPMI-1640, Ham's F-10, and F-12; animal tissue, or a subject's body. In some embodiments, the nanomedicinal composition releases greater than 50 wt %, preferably greater than 52.5 wt %, preferably greater than 55 wt %, preferably greater than 57.5 wt %, preferably greater than 60 wt %, preferably greater than 62.5 wt %, preferably greater than 65 wt %, preferably greater than 67.5 wt %, preferably greater than 70 wt %, preferably greater than 72.5 wt %, preferably greater than 75 wt %, preferably greater than 77.5 wt %, preferably greater than 80 wt % of a total weight of the anti-cancer therapeutic.

In some embodiments, the antioxidant is provided as an outer component of the nanomedicinal composition. As an outer component the antioxidant is mainly located or disposed at an outside surface of particles of the nanomedicinal composition. The position of the antioxidant mainly at the surface or enriched at the surface can be achieved by treating a composition that contains the porous silicate and/or aluminosilicate matrix, the cerium oxide nanoparticles and the anti-cancer therapeutic with antioxidant particles or, preferably, a solution comprising an antioxidant agent. Subsequent drying of the resultant particles preferentially disposes the antioxidant at an exterior portion of particles of the nanomedicinal composition. In other embodiments the antioxidant is present throughout the nanomedicinal composition and, in addition, is a main component of the exterior surface of the nanomedicinal composition. This structure of the nanomedicinal composition is obtained by preparing a nanomedicine medicinal composition containing the porous silicate and/or aluminosilicate matrix, cerium oxide nanoparticles, anti-cancer therapeutic, and antioxidant in particulate form then treating the resulting particulate material with a solution of the same antioxidant or a second antioxidant to place the antioxidants at an exterior and/or surface location of the nanomedicinal composition.

Placing the antioxidant at a surface position of particles of the nanomedicinal composition provides an important benefit. One aspect that may be positively affected is the release rate of the pharmaceutical agent mixture. The antioxidant may inhibit release of the pharmaceutical agent mixture for a time period while the nanomedicinal composition travels through the vascular system of a patient undergoing treatment. This provides an induction period during which only minor amounts of the pharmaceutical agent mixture are released. The release of the pharmaceutical agent mixture may be facilitated by an acidic pH at a tumor site. Such facilitation may, for example, take the form of an increased rate of release, an increased total amount released, or both.

In this aspect of the invention the release of the pharmaceutical agent may be due over a release period of at least 2 hours, preferably at least 4 hours, preferably at least 6 hours, preferably at least 8 hours, preferably at least 10 hours, preferably at least 12 hours, preferably at least 14 hours, preferably at least 16 hours, preferably at least 18 hours, preferably at least 20 hours Initial release rates are preferably 10 wt % of the total amount of pharmaceutical agent in the nanomedicinal composition during the induction period. Upon passage of the induction period and arrival of the nanomedicinal composition at a target site, a major portion of the pharmaceutical agent is released. In some embodiments, the major portion comprises at least 25 wt %, preferably at least 30 wt %, preferably at least 35 wt %, preferably at least 40 wt %, preferably at least 45 wt %, preferably at least 50 wt % of a total amount of pharmaceutical agent released.

In some embodiments, the induction period is provided by a coating disposed on the nanomedicinal composition, the coating as described above. In such embodiments, the coating may inhibit the release of the pharmaceutical agent mixture. Removal of the coating by any suitable process, for example by dissolving, degrading, or digesting, may allow the pharmaceutical gent mixture to be released.

In some embodiments, the nanomedicinal composition has an antioxidant release rate of 0.1 to 10 wt % per hour, preferably 0.25 to 9 wt % per hour, preferably 0.5 to 7.5 wt % per hour, preferably 0.75 to 5 wt % per hour, preferably 1 to 4 wt % per hour based on a total initial weight of antioxidant. In such embodiments, the antioxidant release rate may be an average antioxidant release rate measured over the release period as described above. In some embodiments, the nanomedicinal composition has an initial antioxidant release rate which is maintained over an initial release period. In such embodiments, the initial release period may be followed by a second release period which has a second antioxidant release rate. The initial antioxidant release rate and/or second antioxidant release rate may be average release rates as described above. In some embodiments, the nanomedicinal composition has an anti-cancer therapeutic release rate of 0.5 to 15 wt % per hour, preferably 1 to 14 wt % per hour, preferably 2.5 to 13 wt % per hour, preferably 5 to 11 wt % per hour, preferably 6 to 10 wt % per hour based on a total initial weight of anti-cancer therapeutic. In such embodiments, the anti-cancer therapeutic release rate may be an average anti-cancer therapeutic release rate measured over the release period as described above. In some embodiments, the nanomedicinal composition has an initial anti-cancer therapeutic release rate which is maintained over an initial release period. In such embodiments, the initial release period may be followed by a second release period which has a second anti-cancer therapeutic release rate. The initial anti-cancer therapeutic release rate and/or second anti-cancer therapeutic release rate may be average release rates as described above. In some embodiments, the initial release period comprises the first 20 hours of release, preferably the first 18 hours of release, preferably the first 16 hours of release, preferably the first 14 hours of release, preferably the first 12 hours of release, preferably the first 10 hours of release. Such "first hours of release" are preferably measured from the initiation of release. The initiation of release may be measured by, for example a delivery of the nanomedicinal composition to a tumor site or a pre-determined amount of time after administration. Such a pre-determined time may be any suitable amount of time known to one of ordinary skill in the art, for example, an expected time for delivery of the nanomedicinal composition to the tumor site, an expected circulation time, an expected coating degradation time, or the like.

The present disclosure also relates to a method of forming the nanomedicinal composition, the method comprising mixing a cerium salt with the porous inorganic matrix to form a powdery mixture, calcining the powdery mixture to form the nanocarrier, mixing the nanocarrier and the antioxidant in an impregnation solution thereby forming an antioxidant-loaded nanocarrier, and mixing the antioxidant-loaded nanocarrier and the platinum (II) complex in an aqueous solution thereby forming the nanomedicinal composition. In some embodiments, the calcining is performed at a temperature of 200 to 500° C., preferably 225 to 475° C., preferably 250 to 450° C., preferably 275 to 425° C., preferably 300 to 400° C., preferably 325 to 375° C., preferably 340 to 360° C., preferably 350° C. The calcining step may be carried out under air, nitrogen, argon or a combination thereof. The mixture of gas may be 60% to 100%, or 70% to 90% nitrogen and 0% to 80%, 10% to 70%, or 30% to 50% argon. In preferred embodiments, the calcining is performed in ambient air. In some embodiments, the calcining is performed for 0.25 to 12 hours, preferably 0.5 to 10 hours, preferably 1 to 9 hours, preferably 1.5 to 8.5 hours, preferably 2 to 8 hours, preferably 2.5 to 7.5 hours, preferably 3 to 7 hours, preferably 3.5 to 6.5 hours, preferably 4 to 6 hours, preferably 4.5 to 5.5 hours, preferably 5 hours.

In some embodiments, the impregnation solution comprises an alcohol having 1 to 5 carbon atoms. In some embodiments, the alcohol having 1 to 5 carbon atoms is methanol. In some embodiments, the impregnation solution comprises water. In some embodiments, the impregnation solution comprises glycerol. In some embodiments, the antioxidant is present in the impregnation solution in an amount of 1 to 7.5 mg/mL of impregnation solution, preferably 1.5 to 6.5 mg/mL, preferably 2 to 6 mg/mL, preferably 2.5 to 5.5 mg/mL, preferably 3 to 5 mg/mL, preferably 3.25 to 4.75 mg/mL, preferably 3.5 to 4.5 mg/mL, preferably 3.75 to 4.25 mg/mL, preferably 3.9 to 4.1 mg/mL, preferably 4 mg/mL. In some embodiments, the nanocarrier is present in the impregnation solution at a concentration of 2 to 30 mg/mL, preferably 4 to 28 mg/mL, preferably 6 to 26 mg/mL, preferably 8 to 24 mg/mL, preferably 10 to 22 mg/mL, preferably 12 to 20 mg/mL, preferably 13 to 19 mg/mL, preferably 14 to 18 mg/mL, preferably 15 to 17 mg/mL, preferably 16 mg/mL.

In some embodiments, the aqueous solution is a saline. In preferred embodiments, the aqueous solution is phosphate buffered saline. In some embodiments, the platinum (II) complex is present in the aqueous solution at a concentration of 0.5 to 5 mg/mL, preferably 1 to 4.5 mg/mL, preferably 1.5 to 4.25 mg/mL, preferably 2 to 4 mg/mL, preferably 2.25 to 3.75 mg/mL, preferably 2.5 to 3.5 mg/mL, preferably 2.75 to 3.25 mg/mL, preferably 2.9 to 3.1 mg/mL, preferably 3 mg/mL of aqueous solution. In some embodiments, the antioxidant-loaded nanocarrier is present in the aqueous solution at a concentration of 20 to 100 mg/mL, preferably 30 to 90 mg/mL, preferably 35 to 85 mg/mL, preferably 40 to 80 mg/mL, preferably 45 to 75 mg/mL, preferably 50 to 70 mg/mL, preferably 55 to 65 mg/mL, preferably 60 mg/mL.

The present disclosure also relates to a method for treating a cancer in a subject, the method comprising administering to a subject in need of therapy a pharmaceutical composition comprising the nanomedicinal composition. The cancer is at least one selected from the group consisting of breast cancer, colorectal cancer, and lung cancer. In preferred embodiments, the cancer is breast cancer. The pharmaceutical composition may further comprise one or more pharmaceutically acceptable carriers.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it contains. The term "carrier" encompasses any excipient, binder, diluent, filler, salt, buffer, solubilizer, lipid, stabilizer, or other material well-known in the art for use in pharmaceutical formulations. The choice of a carrier for use in a pharmaceutical composition will depend upon the intended route of administration for the pharmaceutical composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) peptides; proteins, such as serum albumin, gelatine, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrin; chelating agents such as EDTA; sugar alcohols such as mannitol or sorbitol; salt-forming counter ions such as sodium; and/or non-ionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatine, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), C12-C16 fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethyl-ammonium bromide, tetradecyltrimethylammonium bromide, tetradecyltrimethylammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphos-phazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the pharmaceutical composition may be in the form of solid dosage form such as tablets, caplets, capsules, powders, and granules, semi-solid dosage form such as gels, pastes, and suppositories, liquid dosage forms such as suspension, and dispersions, inhalation dosage form such as aerosols, sprays, and powders.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatine, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, suspensions, syrups, and elixirs containing inert diluents commonly used in the art, such as water. Such pharmaceutical compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection dispersions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These dispersions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable dispersion or suspension in a non-toxic parenterally acceptable diluent or solvent, for example, in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethylacetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug. Such suppositories may be advantageous for treating colorectal cancer, but may be unsuitable for treating other cancers.

Administration by inhalation may be advantageous for treating lung cancer, but may be unsuitable for treating other cancers.

In other embodiments, the pharmaceutical composition comprising the nanomedicinal composition disclosed herein thereof has different release rates categorized as immediate release and controlled- or sustained-release.

As used herein, the terms "treat", "treatment", and "treating" in the context of the administration of a therapy to a subject in need thereof refers to the reduction or inhibition of the progression and/or duration of a disease (e.g. cancer), the reduction or amelioration of the severity of the disease, and/or the amelioration of one or more symptoms thereof resulting from the administration of one or more therapies.

"Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the pharmaceutical compositions according to the present disclosure is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. White women or a person with (i) certain inherited genes (e.g. mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) smoke or regularly breathe in second-hand smoke, (ii) exposed to carcinogens including, but not limited to polycyclic aromatic hydrocarbons (e.g. benzo[a]pyrene, benz[a]anthracene, and methylated derivatives thereof), asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), and rectal administration. Those of ordinary skill in the art are familiar with administration techniques that can be employed with the compounds and methods described herein. In preferred embodiments, the active ingredient and/or the pharmaceutical composition described herein are administered orally.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", "pharmaceutically effective amount" or "sufficient amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In some embodiments, an effective amount is in the range of 0.1-30 g/kg of the nanomedicinal composition per body weight of the subject.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be before or after the composition is administered.

A treatment method may comprise administering the pharmaceutical composition of the current disclosure as a single dose or multiple individual divided doses, wherein the nanomedicinal composition is accumulated and releases the loaded anti-cancer therapeutic and/or antioxidant in or nearby the diseased tissues. In some embodiments, the pharmaceutical composition is administered at various dosages (e.g. a first dose with an effective amount of nanomedicinal composition comprising 200 mg of the anti-cancer therapeutic per kilogram of the subject and a second dose with an effective amount of the nanomedicinal composition comprising 50 mg of the anti-cancer therapeutic per kilogram of the subject). In some embodiments, the interval of time between the administration of the pharmaceutical composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the pharmaceutical composition is administered once daily for at least 2 days, 5 days, 6 days, or 7 days. In certain embodiments, the pharmaceutical composition and one or more additional therapies are administered less than 1 day, 1 week, 2 weeks, 3 weeks, 4 weeks, 1 month, 2 months, 3 months, 6 months, 1 year, 2 years, or 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In most embodiments of treatment, the method further comprises measuring a concentration of a biomarker and/or detecting a mutation in a biomarker before and/or after the pharmaceutical composition comprising the nanomedicinal composition of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for breast cancer include, without limitation, BRCA1, BRCA2, HER-2, estrogen receptor, progesterone receptor, CA 15-3, CA 27.29, CEA, Ki67, cyclin D1, cyclin E, and ERβ. Potentially predictive cancer biomarkers include, without limitation, mutations in genes BRCA1 and BRCA2 for breast cancer and/or ovarian cancer, overexpression of CEA, NSE, CYFRA-21-1, CA-125, and CA-199 for lung cancer, overexpression of TYMS, mutations in genes p53 and KRAS for colon cancer.

The mutation in the biomarker may be detected by any suitable procedure known to one of ordinary skill in the art, such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, the concentration of the biomarker is measured before and after the administration. When the concentration of the biomarker is maintained, the method may further comprise increasing the effective amount of the nanomedicinal composition by at least 5%, at least 10%, or at least 30%, up to 50%, up to 60%, or up to 80% of an initial effective amount nanomedicinal composition that contains in the range of 1-300 mg of the anti-cancer therapeutic per kilogram of the body weight of the subject. The increased effective amount may be in a range of 1.05-540 mg/kg, preferably 15-420 mg/kg, more preferably 25-270 mg/kg. The subject may be administered with the increased dosage for a longer period (e.g. one more week, 2 more weeks, or 2 more months) than the duration prescribed with the initial effective amount.

In some embodiments, the mutation in the biomarker is detected before administering the pharmaceutical composition to identify subjects predisposed to the disease. For example, subjects with a BRCA1 germline mutation are at a higher risk of contracting breast cancer, or ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

The examples below are intended to further illustrate protocols for preparing, characterizing, and using the nanomedicinal composition or for treating a cancer using the nanomedicinal composition and are not intended to limit the scope of the claims.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

EXAMPLES

Monodisperse silica (particle size of 80 nm) was supplied by Superior silica, USA. Halloysite as Hal (kaolin clay) with formula $Al_2Si_2O_5$ $(OH)_4·2H_2O$ was obtained from Sigma-Aldrich. Cerium nitrate hexahydrate (99.5%) from Molequle-On (New Zealand) was used as the source for $CeO_2$NPs. Anticancer drug (cisplatin) and antioxidant (curcumin) were purchased from Sigma Aldrich and Molequle-On.

Synthesis of 5 wt % $CeO_2$/Silica

The nanocomposite was prepared by wet impregnation technique. 0.155 g of cerium nitrate hexahydrate was taken and dissolved in 30 ml of water. After stirring for 10 min, 1 g of silica was added and stirred overnight. Then the solution was dried at 120° C. for 6 h and finally calcined at 350° C. for 5 h at 2° C./min. Similarly, $CeO_2$/Hal was prepared by a similar method, where silica was replaced with halloysite.

Synthesis of 5 wt % $CeO_2$/Silica/Cp/Cur

In the first step, curcumin was loaded on silica. 40 mg of curcumin was dissolved in 10 ml of methanol for 10 min. Then 160 mg of silica was added, and the mixture was sonicated for 2 min. Then the solvent was evaporated using rotary evaporator at 50° C. In second step, cisplatin was functionalized. Cisplatin (30 mg) was first added in normal saline solution (10 ml) and stirred to form a clear solution. Then, $CeO_2$/Silica/Cur (600 mg) was added and stirred overnight under ice cold dark environment. The solution was then filtered, washed, and dried. The functionalized cisplatin was estimated using UV-visible spectroscopy at 208 nm.

Synthesis of 5 wt % $CeO_2$/Hal/Cur 40 mg of curcumin was dissolved in 10 ml of methanol for 10 min. Then 160 mg of halloysite clay was added and the mixture was sonicated for 2 min. Then the solvent was evaporated using rotary evaporator at 50° C.

Characterization Techniques

The $CeO_2$ NPs, Hal and Silica phase of carriers were identified using benchtop XRD (Miniflex 600, Rigaku, Japan). The textural features of nanocomposites were measured using nitrogen adsorption technique (ASAP-2020 plus, Micromeritics, USA). The $CeO_2$ nanoparticle chemical coordination was analyzed using DRS-UV-visible spectroscopy analysis (JASCO, Japan). The morphological variations of nanocarriers after $CeO_2$ loadings were investigated using Scanning electron microscopy (SEM, Inspect S50, FEI, at 20 kV) was performed in order to study the overall morphology and transmission electron microscopy (TEM, Morgagni 268, FEI at 80 kV) for detailed morphology and structure of the two prepared composites (5 wt % Ce/Silica/Cp/Cur and 5 wt % Ce/Hal/Cp). Energy dispersive X-rays spectroscopy (EDS) equipped with SEM instrument was performed in order to confirm the presence and distribution of different elements (elemental analysis and elemental composition) of the two as-synthesized composites. For SEM, the samples were coated with gold to improve the image quality and avoid electron charging during scanning the view area.

Cell Culture & Treatment

MCF-7 (Human Breast Cancer) and HFF-1 (Human Foreskin Fibroblasts) cell lines were sub-cultured in DMEM (Dullbecco's Modified Eagle Medium) supplemented with 1% of L-Glutamine, 10% of Fetal Bovine Serum as FBS (Gibco), 1% of Non-Essential Amino Acid (Gibco), and 1% of penicillin and streptomycin. The cells were cultured in a humidified CO2 incubator at 37° C. (Thermoscientific, Waltham, MA). The cells were seeded for in a 96 well plate (Thermo Fisher, Waltham, USA) with 10,000 cells per well. Cells were treated with the listed NP groups for 24, 48, and 72 hours with different concentrations according to the carried drug concentrations: 5 wt % $CeO_2$/Silica/Cp/Cur, 5 wt % $CeO_2$/Hal/Cur, and as controls 5 wt % $CeO_2$/Silica, 5 wt % $CeO_2$/Hal along with curcumin and cisplatin. The cells were tested after 24, 48 and 72 hours using (Thiazolyl Blue Tetrazolium Bromide, MOLEQULE-ON) MTT assay.

TABLE 1

Different concentrations used for treatment in µg/mL.

| Group | $CeO_2$/Silica/Cp/Cur | $CeO_2$/Hal/Cur | $CeO_2$/Silica | $CeO_2$/Hal | Curcumin | Cisplatin |
|---|---|---|---|---|---|---|
| 1 | 25 | 25 | 25 | 25 | 6.25 | 2.5 |
| 2 | 50 | 50 | 50 | 50 | 12.5 | 5 |
| 3 | 100 | 100 | 100 | 100 | 25 | 10 |
| 4 | 200 | 200 | 200 | 200 | 50 | 20 |
| 5 | 400 | 400 | 400 | 400 | 100 | 40 |

Cytotoxicity Assay by MTT

Cultured media along with NPs were removed from 96 well plates and the cells were washed with 1×PBS. Fresh DMEM media was added into each well with 10 µl of MTT ((3-(4,5-dimethylthiazol-2-yl)-2,5-diphenyltetrazolium bromide) from (MOLEQULE-ON) to make a final concentration of 500 µg. The cells were incubated for 3 h at 37° C., then MTT was removed and DMSO (Dimethyl sulfoxide) were added to dissolve the formed formazan dye. The color intensity of the dye was measured using a multiplate reader at 570 nm (Synergy NEO2, Biotek Instruments, Winooski, VT). The results were calculated and compared with the control which has 100% live cells as the percentage of cell viability.

$$\text{Cell Viability (\%)} = \frac{\text{Sample}_{Abs}}{\text{Control}_{Abs}}$$

Imaging by Light Microscope

The cells were observed under the light microscope after each time point to evaluate the morphological changes and study the NPs effect on cell proliferation without fixation. The images were taken by light microscope (TS100F Eclipse, Nikon, Tokyo, Japan) that can work with a digital camera and combined with its Nikon microscope program.

Statistical Analysis

The statistical analysis was done for determining the MTT cytotoxicity assay, using an unpaired two-way ANOVA (GraphPad Prism software), P-value is set at <0.05 (* if P≤0.05,  if P≤0.01, * if P≤0.001, **** if P≤0.0001) were considered statistically significant. The results were calculated from different three experiments.

Characterization of Nanocomposites

X-ray diffraction spectroscopy was used to study the phase structure of silica, Hal and nanocomposites. Silica exhibited the expected amorphous broad peak. The presence of the $CeO_2$ nanoparticles can be confirmed with the marked diffraction peaks corresponding to (111), (200), (220), and (222) planes, indicated with an asterisk in FIG. 1. In contrast to the amorphous silica, Halloysite (Hal) showed characteristic peaks at 2θ=11.8°, 19.9°, 24.8°, 35°, 36°, 38.3° and 55.2°. The diffraction pattern of $CeO_2$ disposed on Hal was rather broad and not far above detection limit. Such low intensity peaks may be indicative of low crystallinity or small particle size of the $CeO_2$ nanoparticles.

Figure 2A:
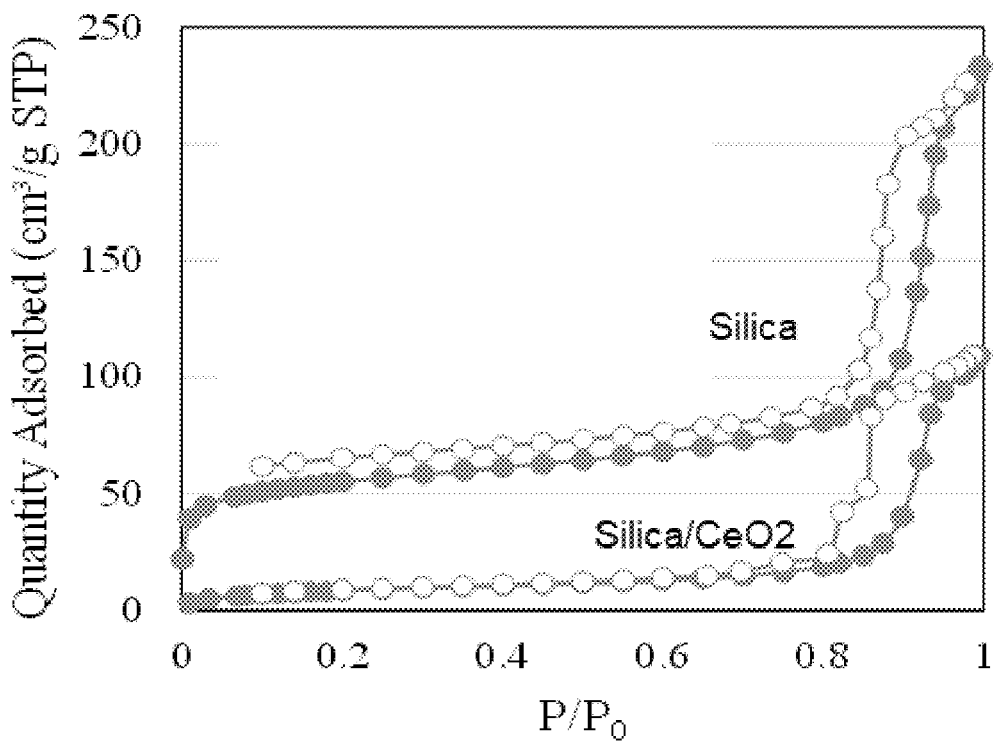
FIG. 2A shows N2 adsorption isotherms of Silica and 5 wt % $CeO_2$/Silica.
Figure 2B:
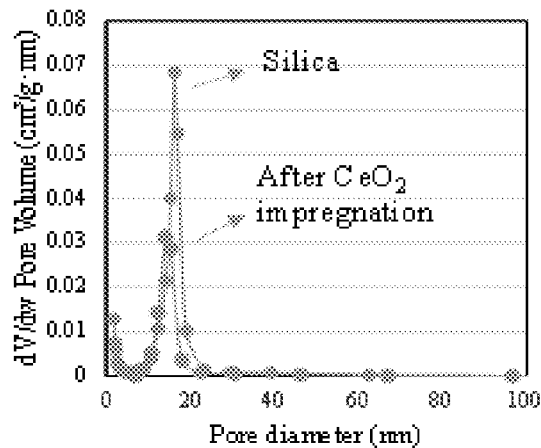
FIG. 2B shows a plot of pore size for Silica and 5 wt % $CeO_2$/Silica.
Figure 3B:
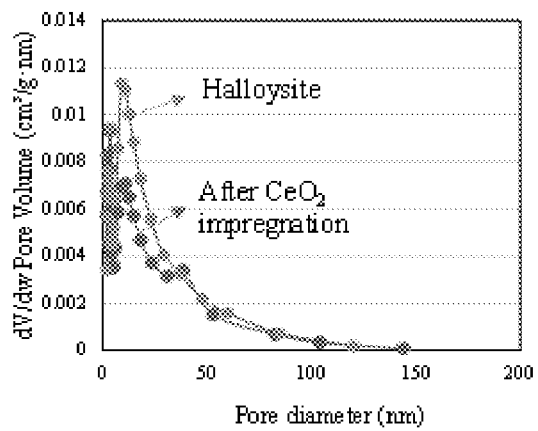
FIG. 3B shows a plot of pore size for Hal and 5 wt % $CeO_2$/Hal.
Figure 3A:
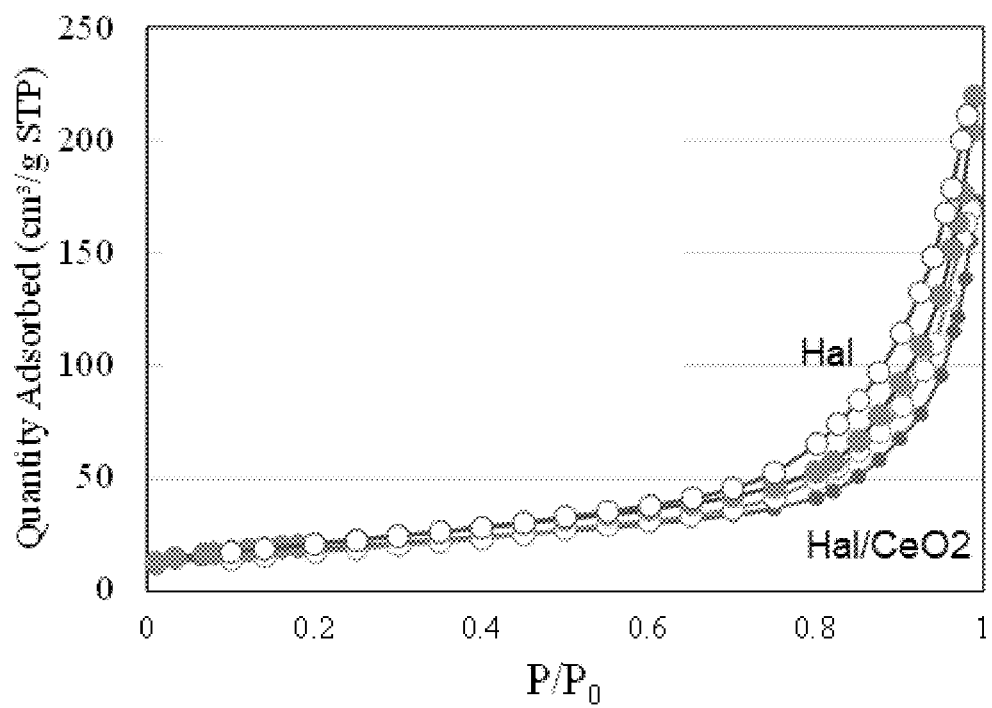
FIG. 3A shows N2 adsorption isotherms of Hal and 5 wt % $CeO_2$/Hal.

The textural properties of like surface area, pore size and pore volume of silica, Hal and $CeO_2$-impregnated samples were analyzed by using nitrogen adsorption isotherm. Parent silica exhibited a type IV isotherm with surface area of 170 $m^2/g$. After $CeO_2$ impregnation, the surface area decreases significantly to 30 $m^2/g$ indicating the surface deposition of $CeO_2$ NPs (FIG. 2A). The pore volume halved from 0.35 $cm^3/g$ to 0.16 $cm^3/g$. An increase in the average pore size distribution from 8.3 nm to 21.8 nm showed the external porous contribution of nanoparticles around the pores (FIG. 2B) The isotherm pattern of Hal and Ce loaded Hal showed a type IV pattern with H3 hysteresis loop (FIG. 3A). In case of Hal, the surface area only slightly decreased after $CeO_2$ deposition from 76 $m^2/g$ to 66 $m^2/g$. The pore volume decreased from 0.34 $cm^3/g$ to 0.26 $cm^3/g$, while average pore size decreased from 17.7 nm to 16 nm (FIG. 3B). This indicates that Hal nanotubes easily accommodate the $CeO_2$ deposition mostly in the interior lumen portion of Hal.

Figure 4:
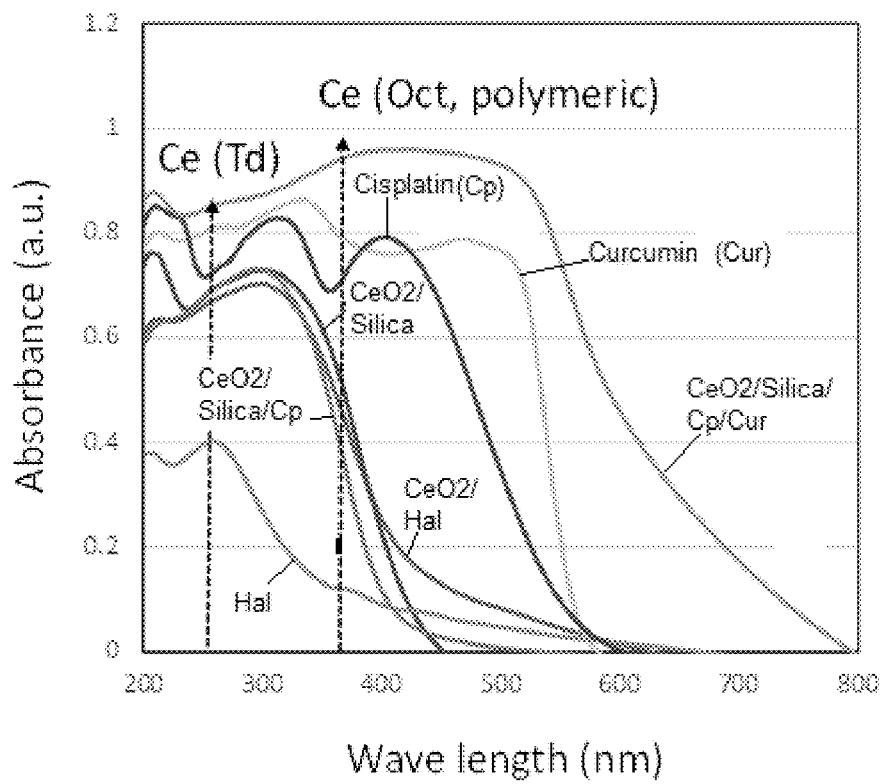
FIG. 4 shows diffuse reflectance spectra of Hal, Cisplatin, Curcumin, 5 wt % $CeO_2$/Silica, 5 wt % $CeO_2$/Hal, 5 wt % $CeO_2$/Silica/Cp, and 5 wt % $CeO_2$/Silica/Cp/Cur.
Figure 5A:
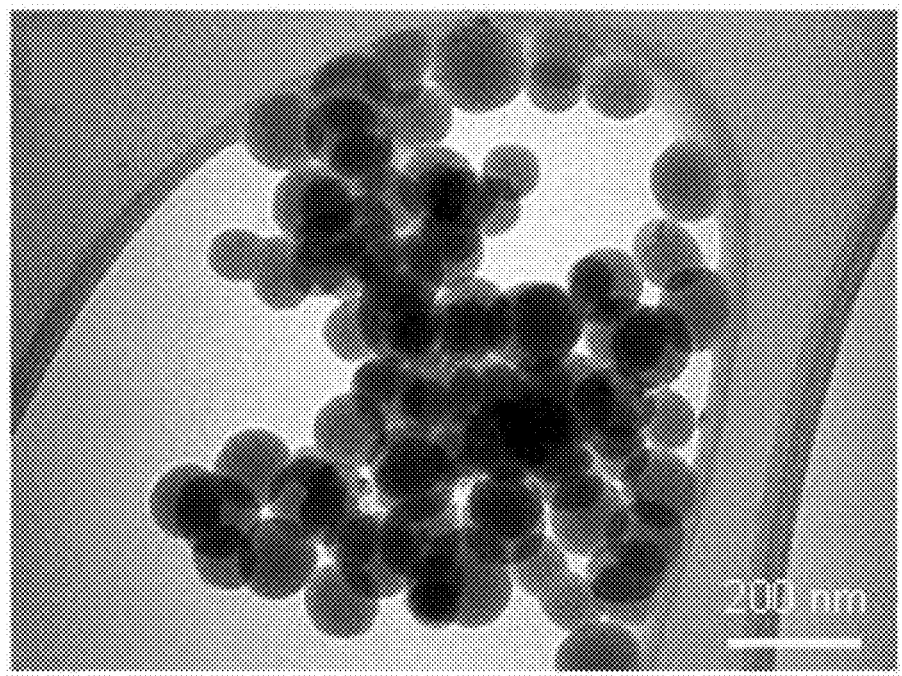
FIGS. 5A-5D are TEM images of the composites at two magnifications, where
Figure 5B:
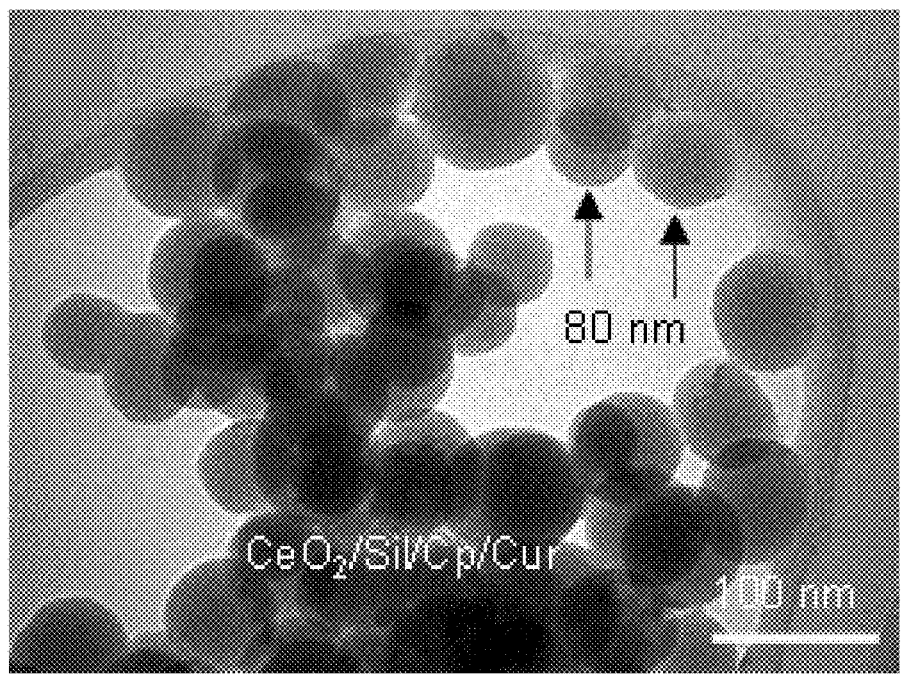
Figure 5C:
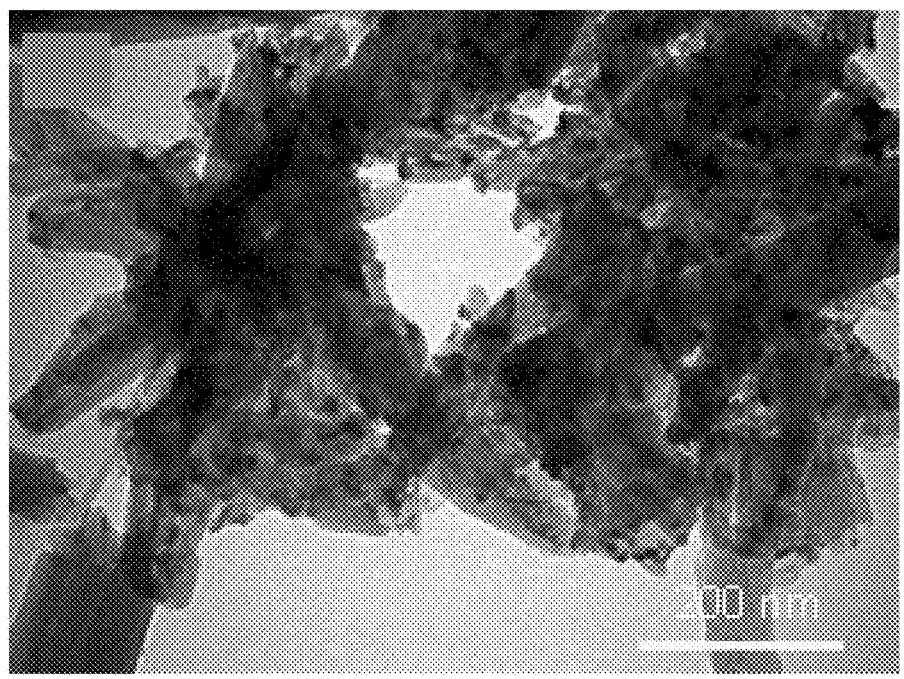
Figure 5D:
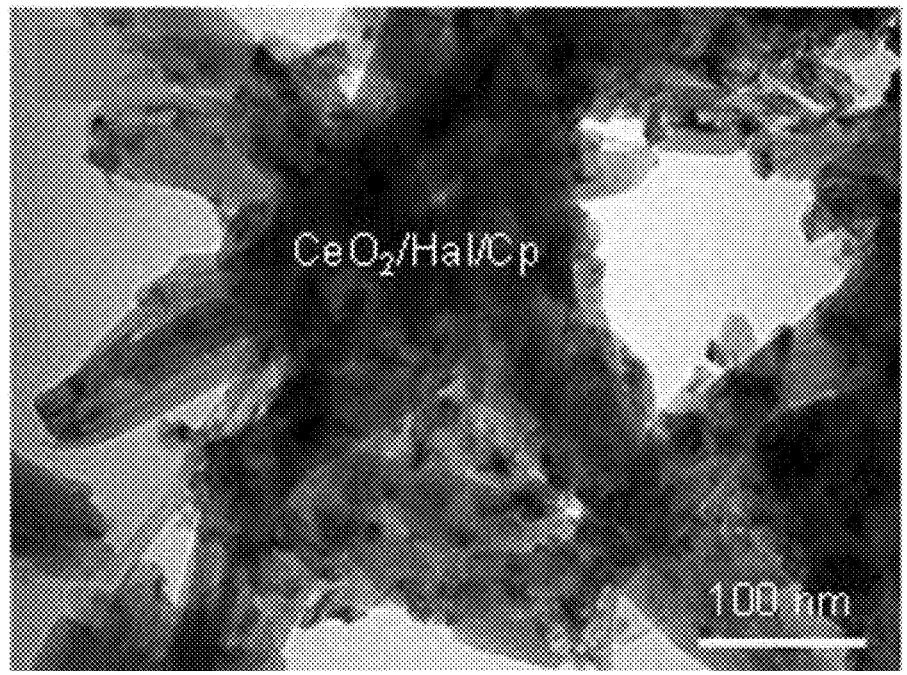

The coordination environment of $CeO_2$ NPs, Curcumin and Cp over Hal and Silica were analyzed using diffuse reflectance spectroscopy. The results are presented in FIG. 4. The Hal support showed an absorption band at about 210 and 260 nm, indicating the framework coordinated aluminum and silica species. The antioxidant curcumin and drug cisplatin revealed broad absorption between 200-600 nm. In case of 5 wt % $CeO_2$/Silica, 5 wt % $CeO_2$/Hal and 5 wt % $CeO_2$/Cp/Silica, after cerium oxide deposition, the spectra absorbance increases with a significantly strong and broad peaks between 250-600 nm. The band at about 250 nm and 300 nm indicates $Ce^{3+}$ and $Ce^{4+}$ ions in tetrahedral coordination, while a band at 380 nm, indicates the octahedral and polymeric cerium species. Cisplatin adsorption was not observed in the nanoformulation. In case of 5 wt % $CeO_2$/Cur/Cp/Silica, the presence of extended absorption mimicking to that of curcumin, indicates presence of curcumin as coating at the external surface of nanoformulation. The morphology and analysis of the two composites ($CeO_2$/Silica/Cp/Cur and $CeO_2$/Hal/Cp) were carried out by using TEM at high resolution. TEM images of the $CeO_2$/Silica/Cp/Cur specimen show the well dispersed spherical shaped silica spheres of around 80 nm NPs (FIG. 5A). High magnification image of the same samples revealed that silica spheres are decorated with $CeO_2$/Cp NPs (FIG. 5B). The average size of these nanoparticles was safely under one digit number. Few silica nanospheres decorated with $CeO_2$/Cp NPs are indicated by black arrows. TEM images of $CeO_2$/Hal/Cp revealed the obvious tubular structure and morphology of the nanoclay (Hal) decorated with spherically shaped $CeO_2$/Hal/Cp nanoparticles (FIGS. 5C-5D). The tubular nature of the clay was determined by a bright contrast of each clay particle as compared to their outer dark parts. The clusters of $CeO_2$/Cp nanoparticles attached with nanoclay were appeared in dark spots here and there, confirming their uniform distribution on clay particles. TEM images of the $CeO_2$/Hal/Cp specimen showed a compact morphology due to less electron-particle contrast, suggesting further an unambiguous coating of $CeO_2$/Cp over Hal nanoclay. Furthermore, the tubular morphology (bright contrast) of the clay/nanoparticles is less visible due to coating of $CeO_2$/Cp as compared to individual clay particles (data is not shown here). In summary, TEM analysis confirmed the successful preparation of two composites; $CeO_2$/Cp/Cur decorated silica nanospheres and $CeO_2$/Cp decorated tubular clays.

Figure 6A:
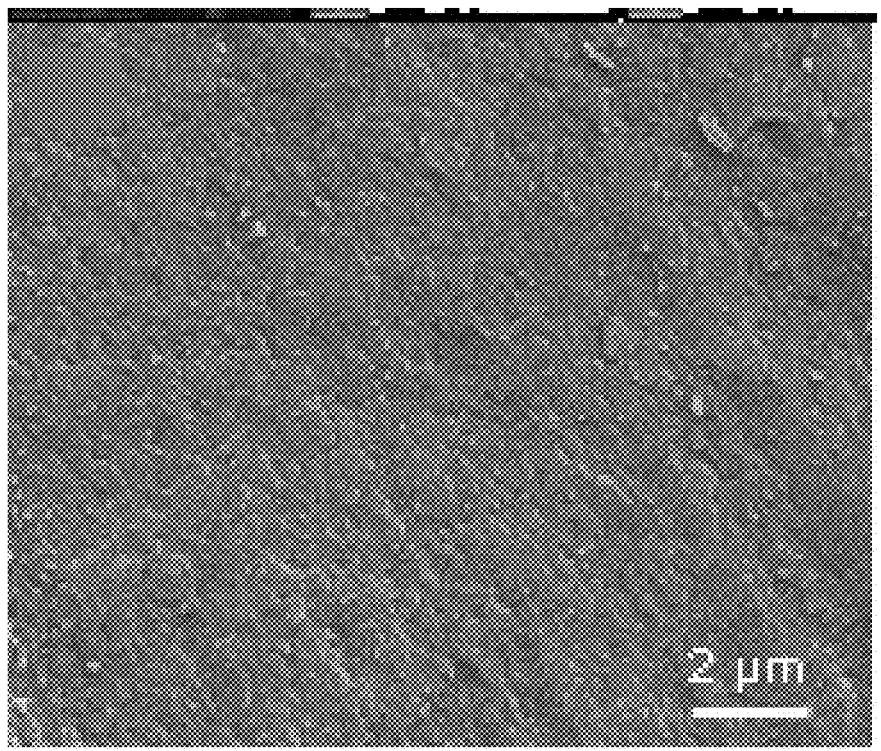
FIGS. 6A-6B are SEM images of the 5 wt % $CeO_2$/Silica/Cp/Cur composite at 20 kX magnification (FIG. 6A) and 40 kX magnification (FIG. 6B).
Figure 6B:
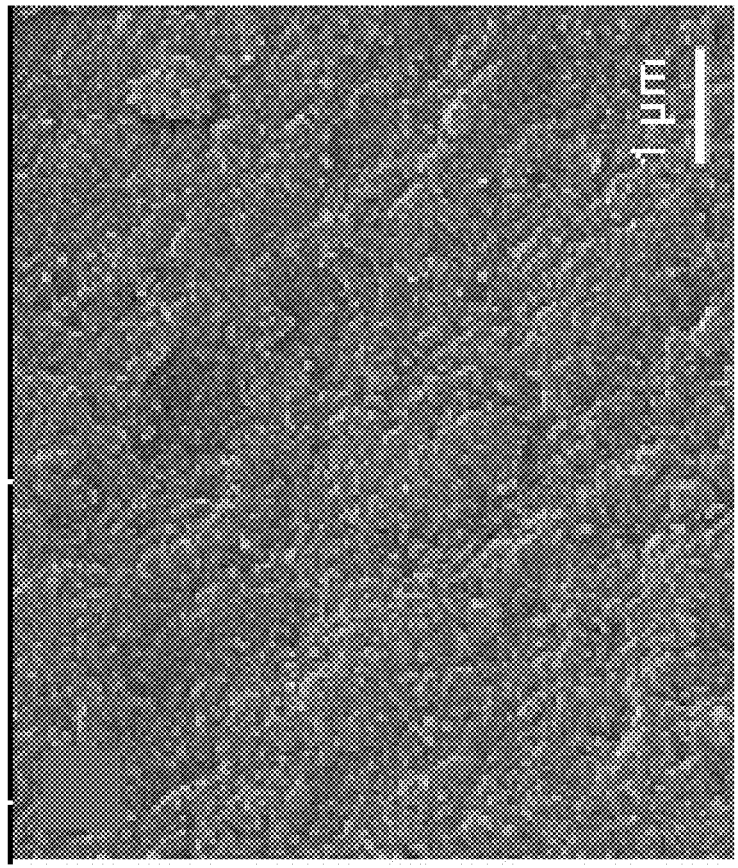
Figure 6C:
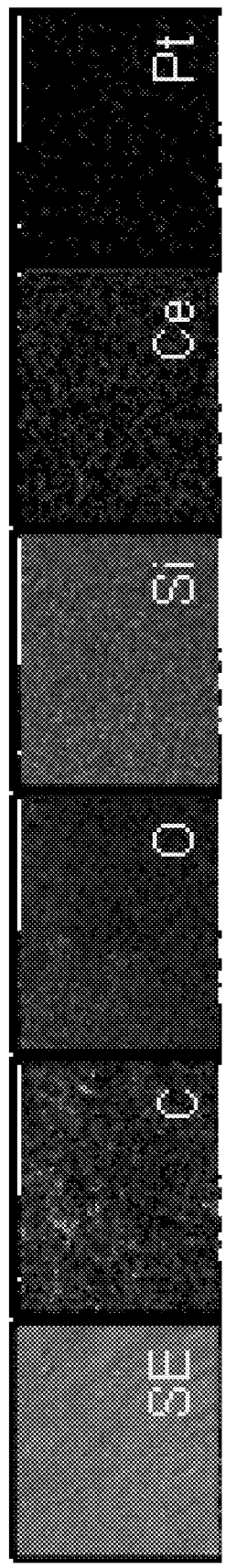
FIG. 6C is an elemental mapping of the 5 wt % $CeO_2$/Silica/Cp/Cur.
Figure 7B:
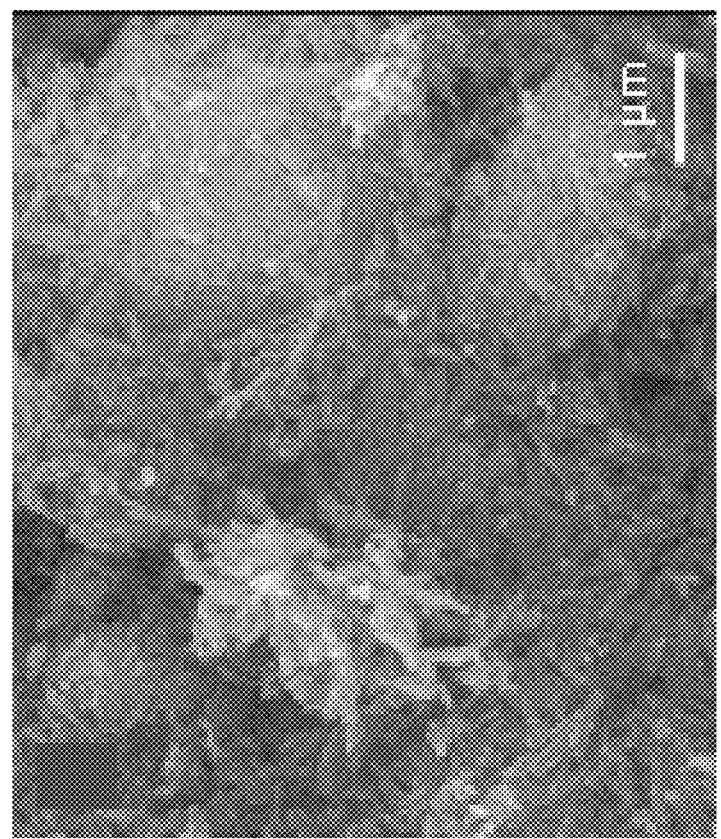
FIGS. 7A-7B are SEM images of the 5 wt % $CeO_2$/Hal/Cp/Cur composite at 20 kX magnification (FIG. 7A) and 40 kX magnification (FIG. 7B).
Figure 7A:
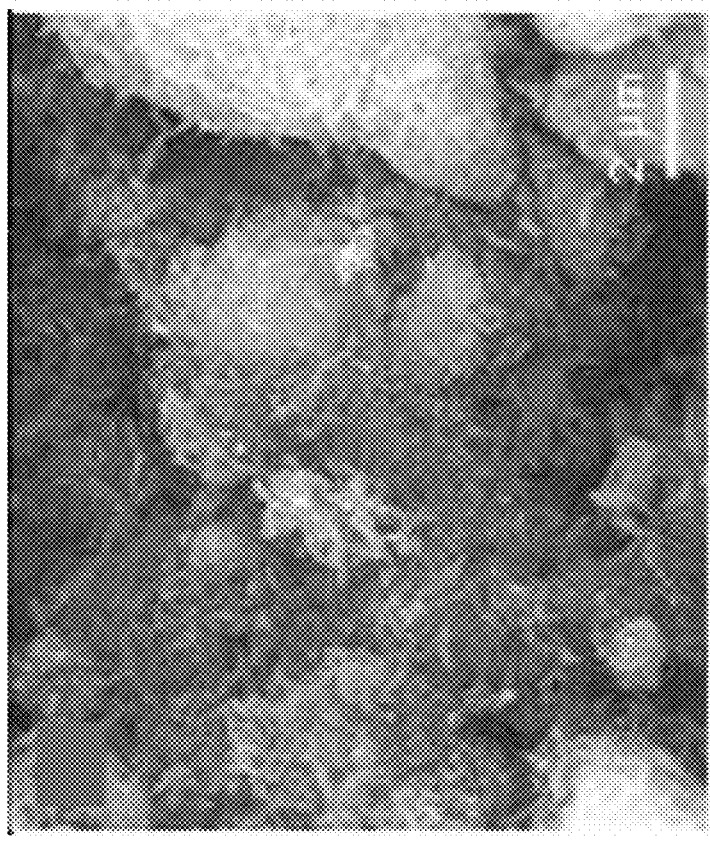
Figure 7C:
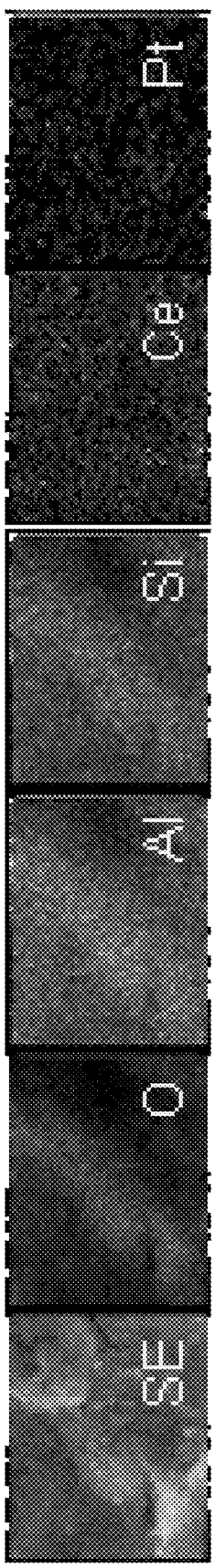
FIG. 7C is an elemental mapping of the 5 wt % $CeO_2$/Hal/Cp/Cur.

SEM imaging, EDS and EDS mapping was further performed to highlight the overall morphology, elemental composition, and distribution of each element. SEM images and elemental mapping of $CeO_2$/Sil/Cp/Cur are shown in FIGS. 6A-6C and for $CeO_2$/Hal/Cp composites in FIGS. 7A-7C, respectively. SEM images showed the smooth morphology of the $CeO_2$/Cp/Cur decorated silica spheres for $CeO_2$/Sil/Cp/Cur specimen (FIGS. 6A-6B) while needle-like morphology was seen for $CeO_2$/Hal/Cp composites (FIGS. 7A-7B). The EDS spectrum of $CeO_2$/Sil/Cp/Cur specimen displayed the following elements: Carbon (C), oxygen (O), silicon (Si), cerium (Ce) and platinum (Pt) from cisplatin. The EDS spectrum of $CeO_2$/Hal/Cp composite exhibited O, Al, Si, Ce and Pt. The EDS mapping images of both the composites $CeO_2$/Sil/Cp/Cur (FIG. 6C) and $CeO_2$/Hal/Cp (FIG. 7C) show uniform colors for Ce and Pt, confirming the uniform distribution of $CeO_2$ and cisplatin nanoparticles over silica spheres and nano clay.

Cytotoxicity Assay of Nanocomposite Treated Cells

Figure 8A:
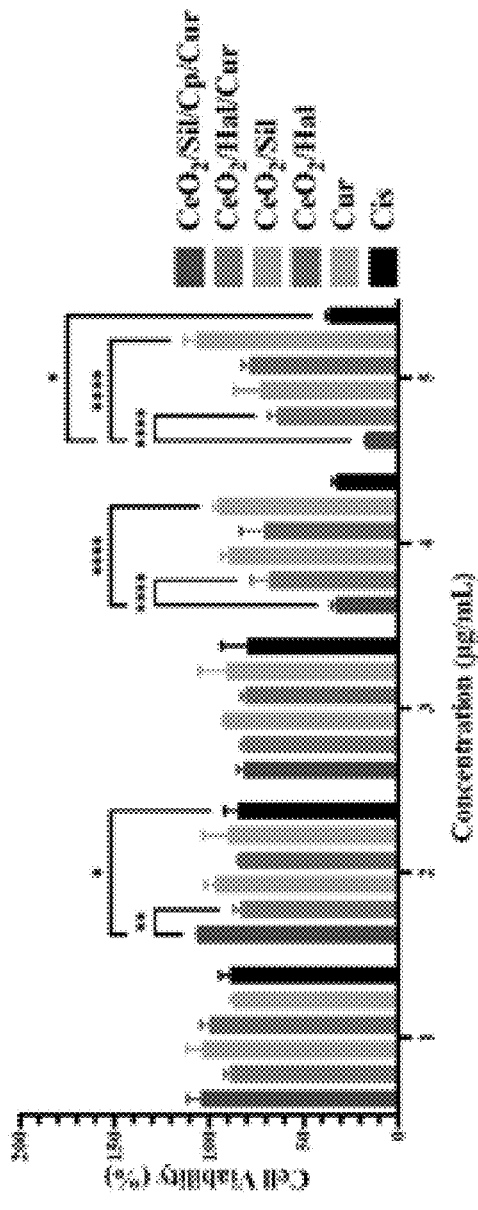
FIGS. 8A-8C are plots of results of the cytotoxicity assay of 5 wt % $CeO_2$/Silica and Hal NPs against MCF-7 cells showing the cell viability % of treated cells with $CeO_2$/Silica/Cp/Cur, $CeO_2$/Hal/Cur, $CeO_2$/Silica, $CeO_2$/Hal, curcumin, and cisplatin for 24 h (FIG. 8A), 48 h (FIG. 8B), and 72 h (FIG. 8C).
Figure 8B:
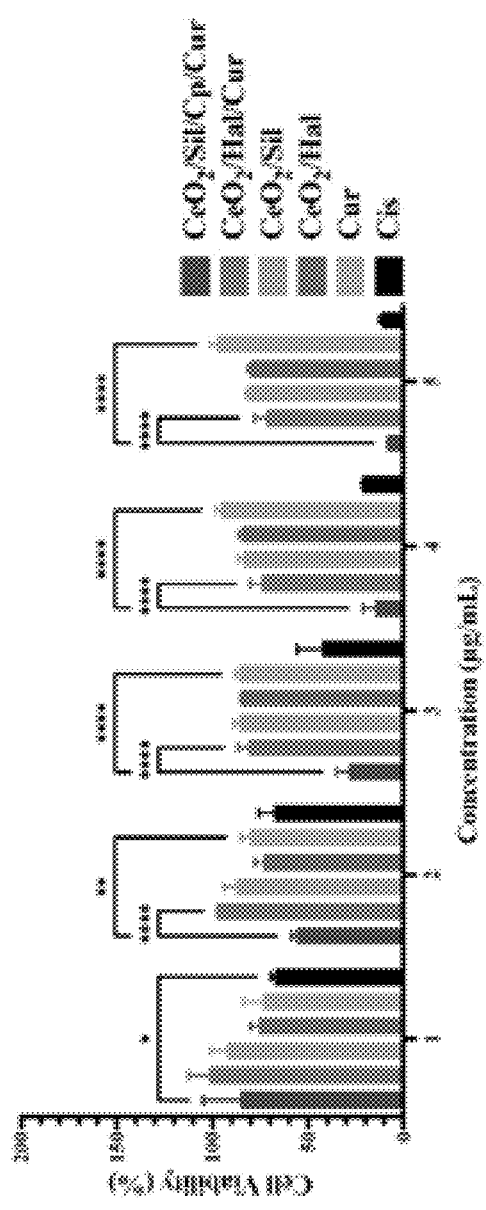
Figure 8C:
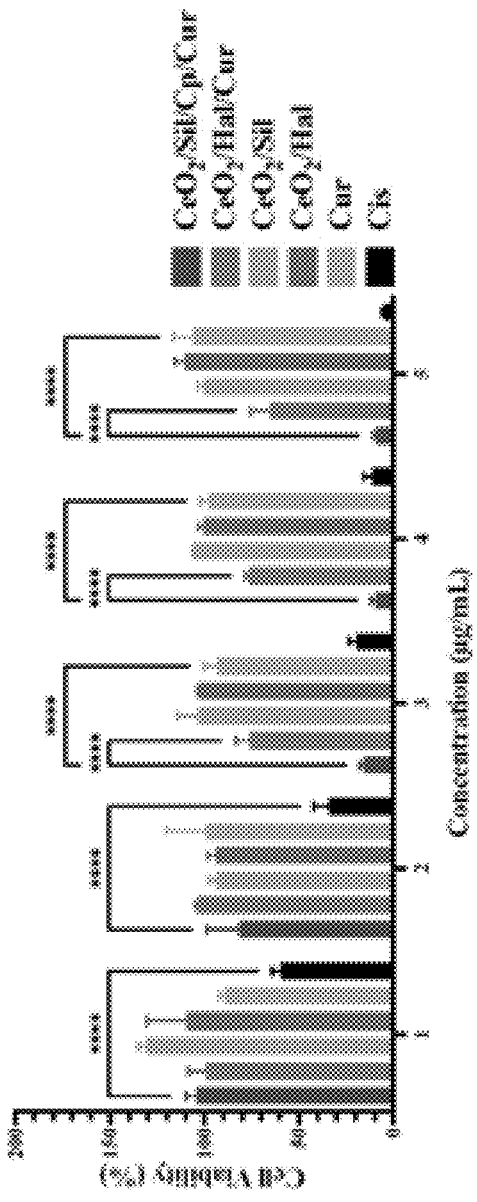

The cytotoxicity study was performed to evaluate the toxicity of $CeO_2$ nanoparticles against breast cancer cell line (MCF-7) and a non-cancerous cell line of human foreskin fibroblast (HFF-1). Different concentrations were applied (see Table 1) for 24, 48 and 72 hours, then, cytotoxicity was measured by MTT assay after each period of treatment. The data were plotted in scattered graphs using excel to calculate the $EC_{50}$ values from the exponential trendline generated equation. The statistical significance with the p value and standard deviation were analyzed by two-way ANOVA test in GraphPad, Prism software. The results indicated that $CeO_2$/Silica/Cp/Cur nanoformulation has proved to have a statistically significant difference of (p<0.0001) in comparison to $CeO_2$/Hal/Cur and curcumin at the highest used concentration where $CeO_2$/Silica/Cp/Cur had resulted in cell viability of 17.6%, 8.0% and 8.5% compared to cisplatin which had resulted in 36%, 11.24% and 5.17% in 24 h, 48 h, and 72 h, respectively. On the other hand, $CeO_2$/Hal/Cur showed less efficacy compared to $CeO_2$/Silica/Cp/Cur and cisplatin against MCF-7 cells. The cytotoxicity of other tested controls of $CeO_2$/Silica and $CeO_2$/Hal nanoparticles showed similar cell viability between 72-78% compared to untreated cells at the highest used concentration in the all-time periods. Interestingly, curcumin showed the lowest efficacy with high cell viability percentages which increased upon used concentration (see FIGS. 8A-8C). In addition, $EC_{50}$ values were calculated to estimate the half maximal cytotoxic effect after each time point. $CeO_2$/Silica/Cp/Cur showed an $EC_{50}$ of 180.4, 114.6, and 49.7 μg/mL obtained from 24 h, 48 h, and 72 h of treatments whereas $CeO_2$/Hal/Cur showed $EC_{50}$ of 599.7, 389.3 and 173.2 μg/mL, respectively which is less efficacy compared to $CeO_2$/Silica/Cp/Cur and cisplatin. A summary of these $EC_{50}$ values is presented in Table 2.

TABLE 3

The half-maximal inhibitory concentrations in μg/mL ($EC_{50}$) of treated MCF-7 cells

| Sample | $EC_{50}$ Value (μg/mL) | | |
|---|---|---|---|
| | 24 h | 48 h | 72 h |
| $CeO_2$/Sil/Cp/Cur | 180.43 | 114.6 | 49.73 |
| $CeO_2$/Hal/Cur | 599.72 | 376.8 | 173.21 |
| Cisplatin (Cp) | 21.58 | 8.03 | 3.12 |

Figure 9A:
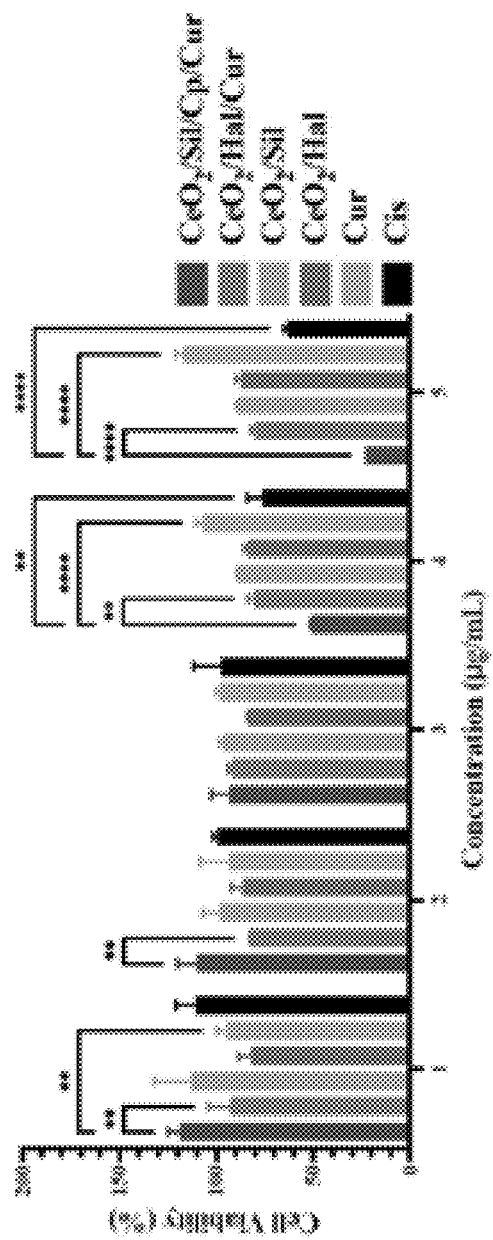
FIGS. 9A-9C are plots of results of the cytotoxicity assay of 5 wt % $CeO_2$/Silica and Hal NPs against HFF-1 cells showing the cell viability % of treated cells with $CeO_2$/Silica/Cp/Cur, $CeO_2$/Hal/Cur, $CeO_2$/Silica, $CeO_2$/Hal, curcumin, and cisplatin for 24 h (FIG. 9A), 48 h (FIG. 9B), and 72 h (FIG. 9C).
Figure 9B:
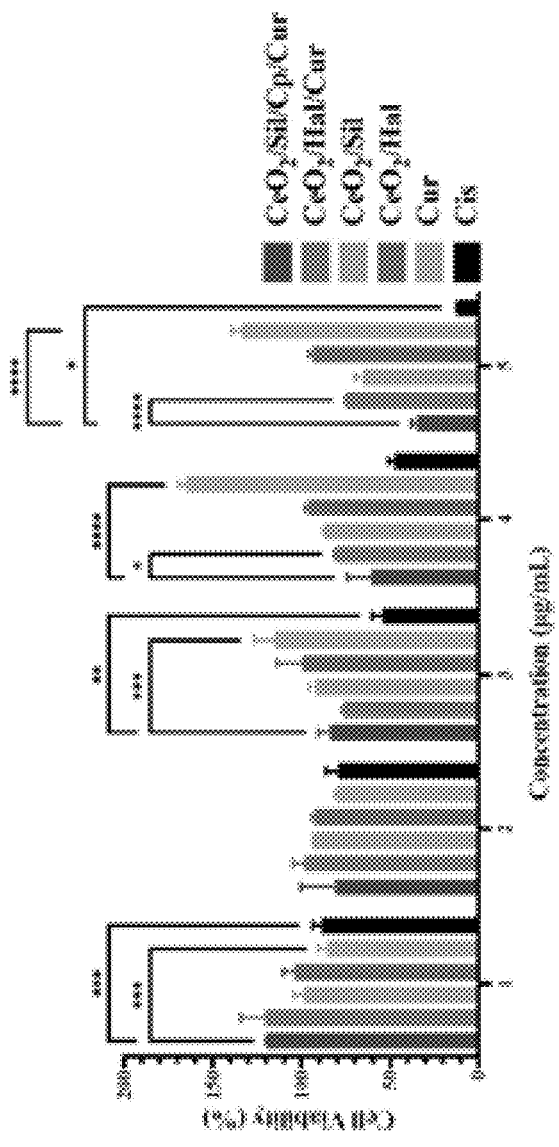
Figure 9C:
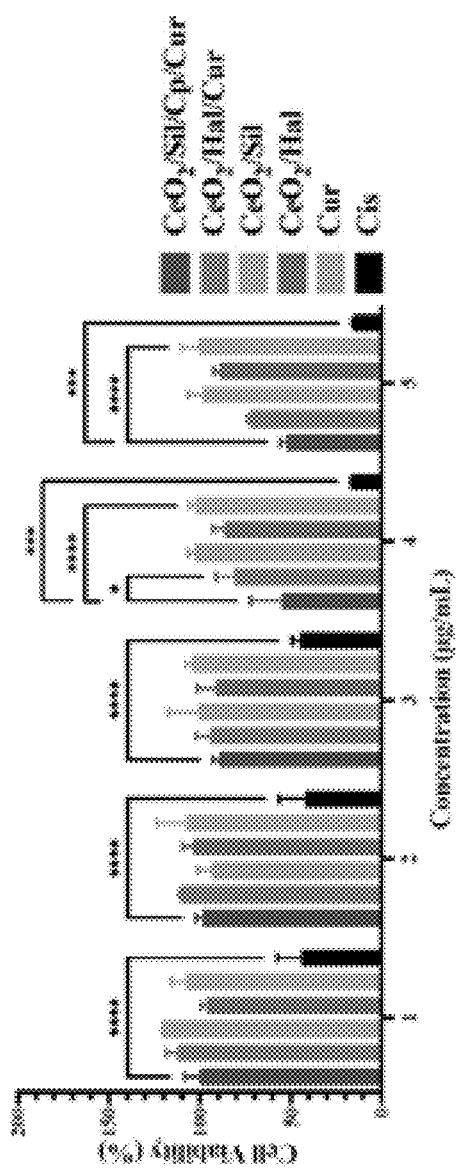

The same groups of treatment were tested against HFF-1 cells to determine the cytotoxicity, $CeO_2$/Silica/Cp/Cur had resulted in cell viability of 23.21%, 34.20% and 52.3% compared to cisplatin which had resulted in 63.25%, 12.02% and 15.31% in 24 h, 48 h, and 72 h, respectively. Similarly, $CeO_2$/Hal/Cur and curcumin showed less efficacy and $CeO_2$/Hal and $CeO_2$/Silica nanoparticles without curcumin or cisplatin showed similar cell viability between 70-87% compared to untreated cells at the highest used concentration in tested time periods (FIG. 9A-9C). The $EC_{50}$ values for $CeO_2$/Silica/Cp/Cur were 254.07, 231.94, and 218.59 μg/mL, and for $CeO_2$/Hal/Cur as 737.92, 651.27 and 432.2 μg/mL in 24 h, 48 h, and 72 h, respectively, which is less efficacy compared to $CeO_2$/Silica/Cp/Cur and cisplatin. A summary of these $EC_{50}$ values is presented in Table 3.

TABLE 3

The half-maximal inhibitory concentrations in μg/mL ($EC_{50}$) of treated HFF-1 cells

| Sample | $EC_{50}$ Value (μg/mL) | | |
|---|---|---|---|
| | 24 h | 48 h | 72 h |
| $CeO_2$/Sil/Cp/Cur | 254.07 | 231.94 | 218.59 |
| $CeO_2$/Hal/Cur | 737.92 | 651.27 | 432.2 |
| Cisplatin (Cp) | 52.3 | 12.62 | 6.58 |

Imaging of Nanocomposite Treated Cells by Light Microscopy

Figure 10A:
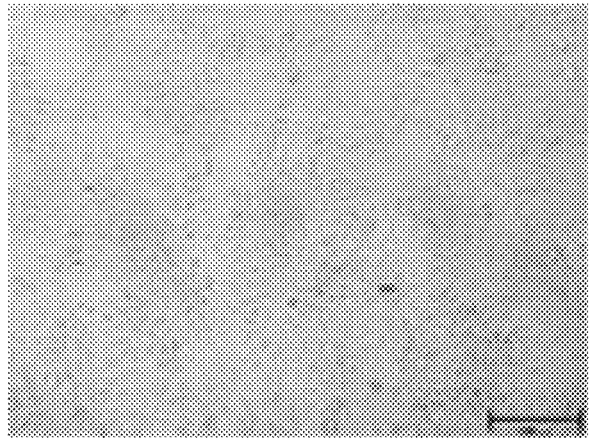
FIGS. 10A-10N show light microscopy images MCF-7 cells which were untreated (FIGS. 10A-10B) and treated with various nanocomposite groups for 48 h as follows: 200 µg/mL of $CeO_2$/Silica/Cp/Cur (FIG. 10C), 400 µg/mL of $CeO_2$/Silica/Cp/Cur (FIG. 10D), 200 µg/mL of $CeO_2$/Hal/Cur (FIG. 10E), 400 µg/mL of $CeO_2$/Hal/Cur (FIG. 10F), 200 µg/mL of $CeO_2$/Silica (FIG. 10G), 400 µg/mL of $CeO_2$/Silica (FIG. 10H), 200 µg/mL of $CeO_2$/Hal (FIG. 10I), 400 µg/mL of $CeO_2$/Hal (FIG. 10J), 200 µg/mL of curcumin (FIG. 10K), 400 µg/mL of curcumin (FIG. 10L), 200 µg/mL of cisplatin (FIG. 10M), and 400 µg/mL of cisplatin (FIG. 10N).
Figure 10B:
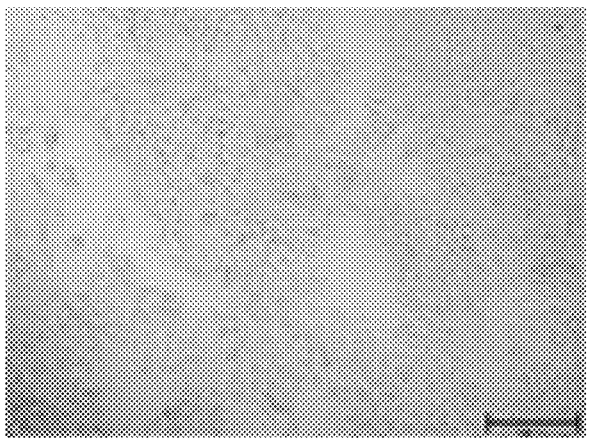
Figure 10C:
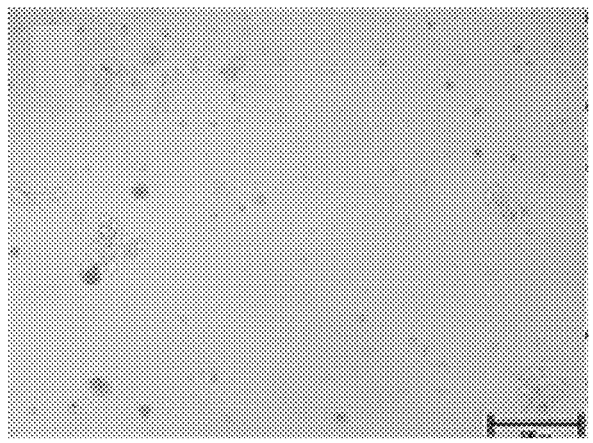
Figure 10D:
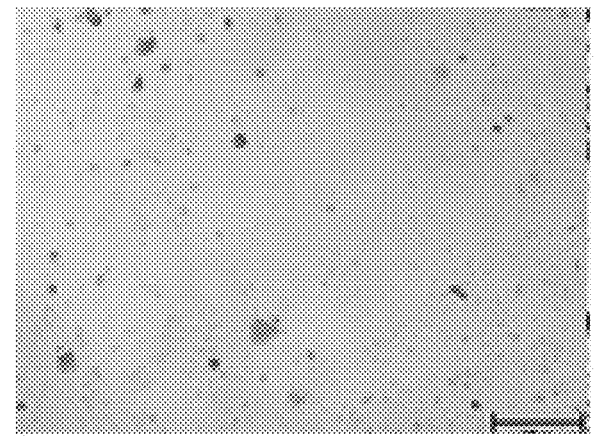
Figure 10E:
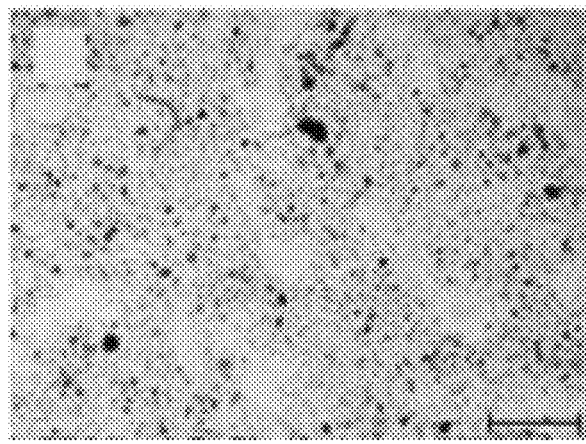
Figure 10F:
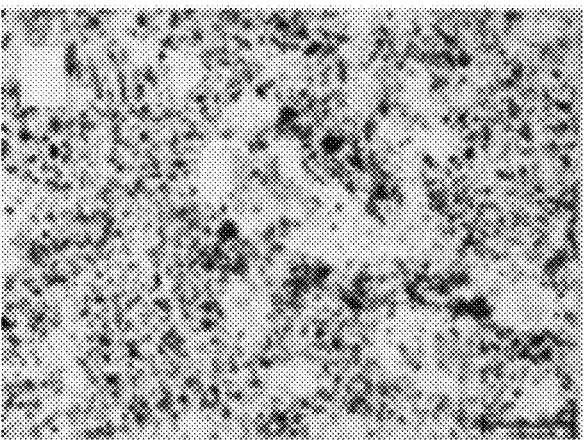
Figure 10G:
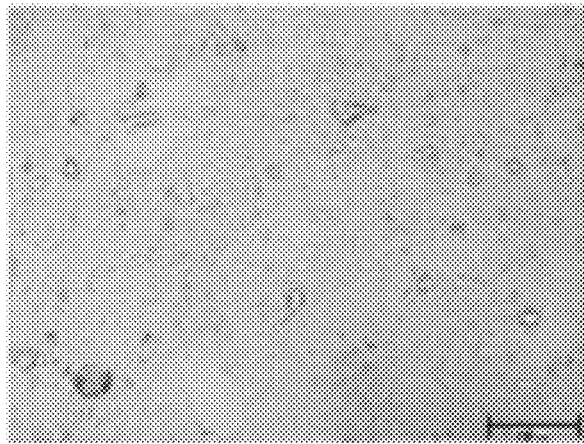
Figure 10H:
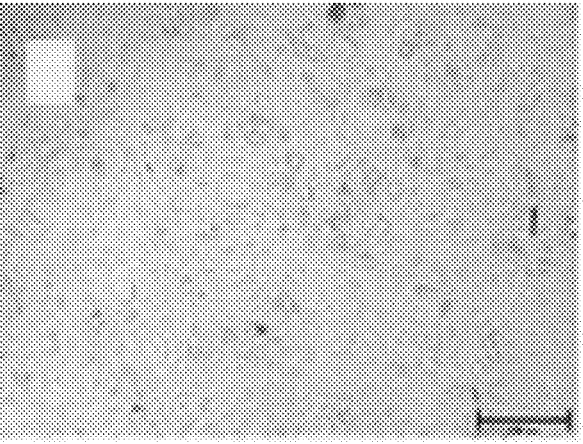
Figure 10I:
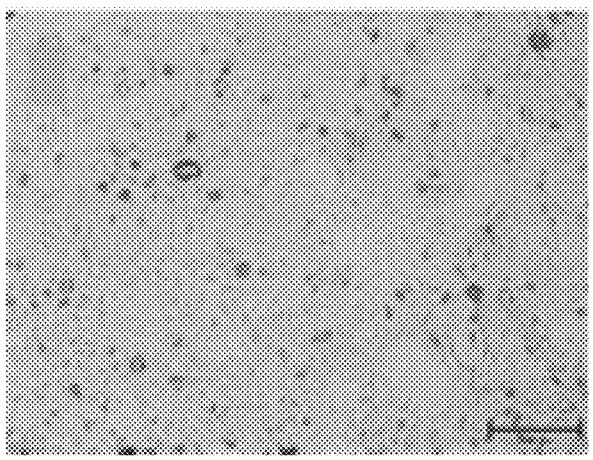
Figure 10J:
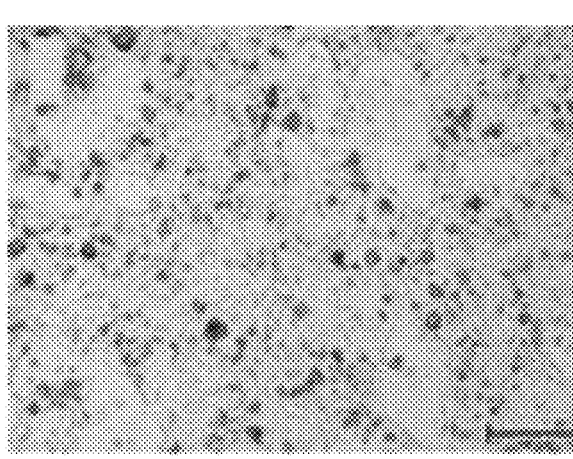
Figure 10K:
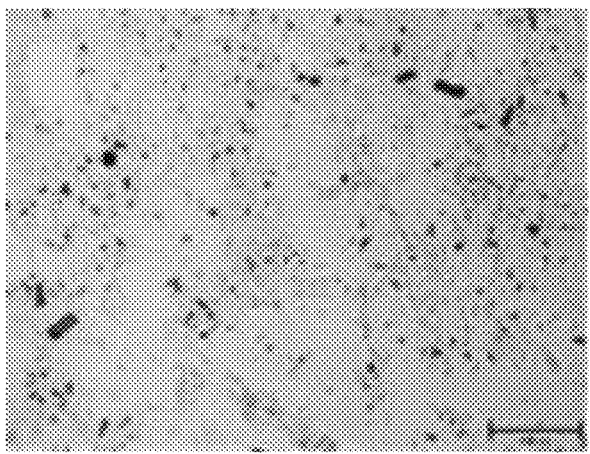
Figure 10L:
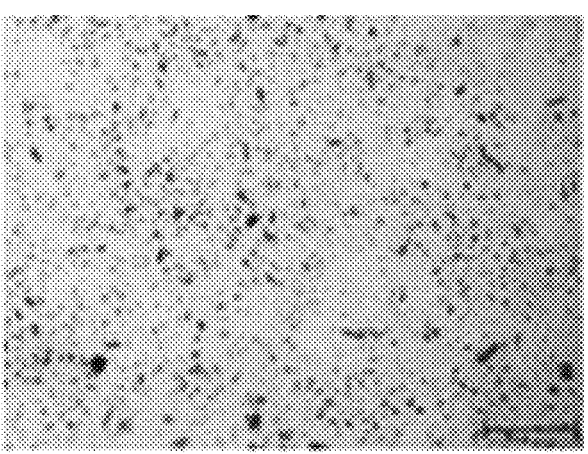
Figure 12:
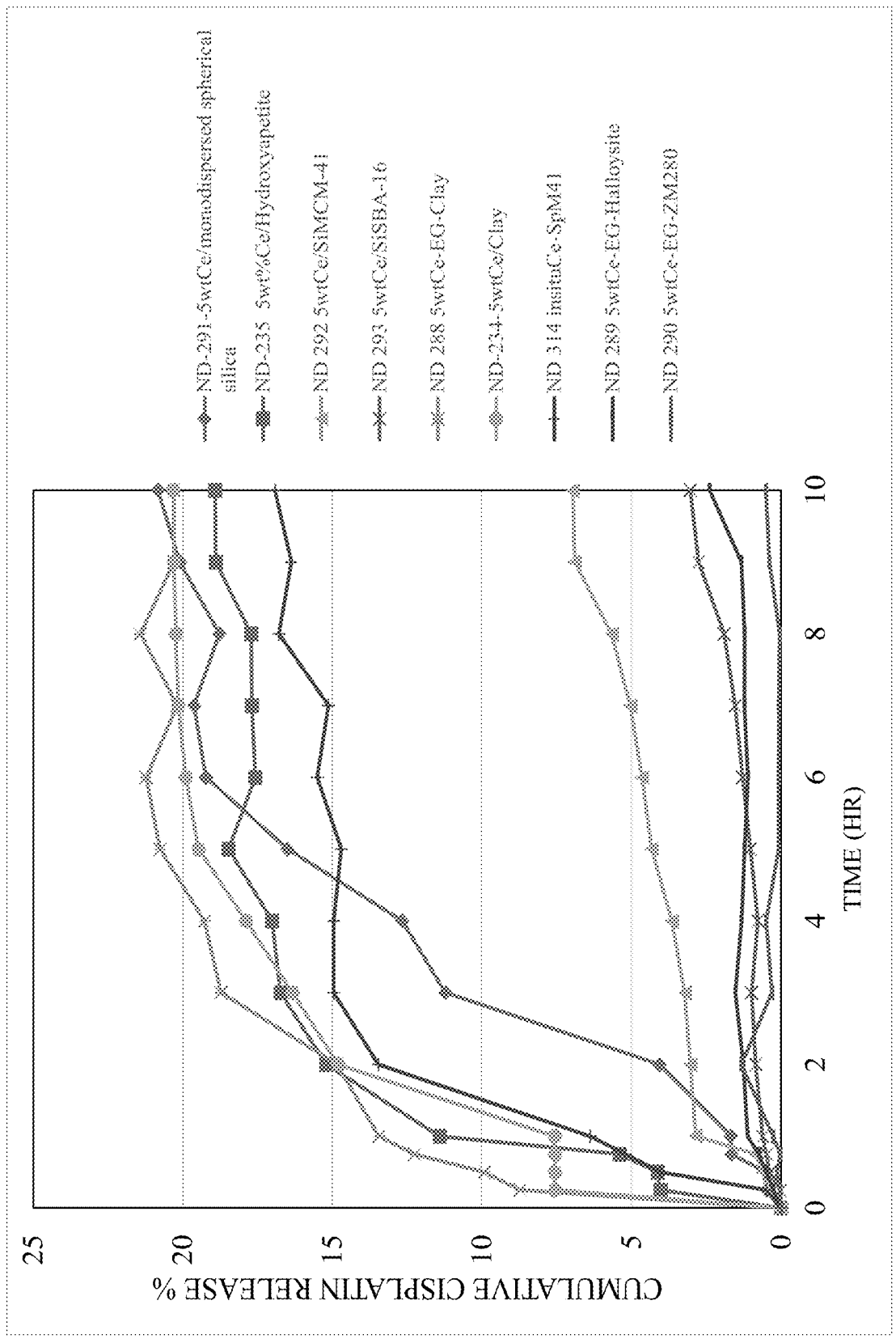
FIG. 12 is a plot of cisplatin drug release profile over different nanocarriers loaded with 5 wt % $CeO_2$ NPs.

The effect of nanocomposites on cell morphology was imaged by using a light microscope after each time point. MCF-7 cells and HFF-1 cells were treated with either 200 or 400 μg/mL for 48 h to evaluate the average morphological changes. Control cells as untreated cells showed normal growth whereas $CeO_2$/Silica/Cp/Cur treated MCF-7 or HFF-1 showed reduction in cell numbers with cell death morphological structures indicated in $CeO_2$/Silica/Cp/Cur as well as cisplatin treated cells (see FIGS. 10A-10N for MCF-7 cells and FIGS. 11A-11N for HFF-1 cells). $CeO_2$/Silica and $CeO_2$/Hal exhibited normal cell proliferation as shown by the viability assay. In addition, $CeO_2$/Hal/Cur and curcumin treated cells were slightly affected upon curcumin compositions and it was hard to detect the morphological changes at 400 μg/mL due to their high nanoparticles background (brownish particles). In the microscopy images, the magnification was ×100 and the scale bar represents 100 μm.

Monodispersed silica and halloysite clay were impregnated with $CeO_2$ NPs. The nature of $CeO_2$ NPs over both supports were analyzed using different physico-chemical techniques. In case of $CeO_2$/Silica, XRD analysis indicated a crystallization of $CeO_2$ NPs with a distinct peak over silica support. Conversely, with halloysite support Hal, a weak diffraction peaks of $CeO_2$ were observed indicating formation of small sized cerium oxide nanoparticles. The textural analysis of parent and after cerium ions deposition showed a significant surface change occurs over silica than with Hal. An increase in silica pore diameter signals an external deposition of NPs around the pores, while deposit inside the lumen part of Hal. $CeO_2$ NPs exhibits a different oxidation states such as $Ce^{3+}$ and $Ce^{4+}$ leading to the possibility of redox reactivity. In cerium oxide nanoparticles, the $Ce^{4+}$ species has been reported to be more prevalent than $Ce^{3+}$, while concentration of both species is related to the overall particle sizes. Small nanoparticles are reported to exhibit more $Ce^{3+}$ species with high free radical scavenging abilities due to more oxygen defect sites than large nanoparticles comprising $Ce^{4+}$ species [Xu, C. and X. Qu, Cerium oxide nanoparticle: a remarkably versatile rare earth nanomaterial for biological applications. NPG Asia Materials, 2014. 6(3): p. e90-e90, incorporated herein by reference in its entirety]. The diffuse reflectance spectra of $CeO_2$/Silica and $CeO_2$/Hal shows the co-existence of both $Ce^{3+}$ and $Ce^{4+}$ species with peaks at 250 nm and 300 nm, respectively). However, the formation of clusters indicates little agglomerations occurs on nanotubes of Hal. The unique oxidation-reduction capability of such cerium oxide nanoparticles with free radical scavenging property gives the nanocomposites the ability to interact with the biological activities of cellular migration and reduces oxidative stress [Wu, H., et al., Ceria nanocrystals decorated mesoporous silica nanoparticle based ROS-scavenging tissue adhesive for highly efficient regenerative wound healing. Biomaterials, 2018. 151: p. 66-77, incorporated herein by reference in its entirety]. The morphological analysis of $CeO_2$/Silica using TEM and SEM analysis clearly shows the monodispersed form of silica with cerium nanoparticles deposition, while $CeO_2$/Hal shows nanotubes with particle dispersions.

The efficacy of Cp and Cur combination against cancer and normal cells were investigated by applying $CeO_2$/Silica/Cp/Cur nanoparticles against MCF-7 and HFF-1 cells, the MTT results showed similar effect to the control free cisplatin indicating that the delivery of cisplatin was successful by $CeO_2$/Silica/Cp/Cur nanoformulation. In addition, the values of $EC_{50}$ were larger in case of $CeO_2$/Silica/Cp/Cur compared to cisplatin suggesting that the loaded curcumin has slightly reduced the side effect of cisplatin. On the other hand, curcumin group, $CeO_2$/Hal/Cur nanoparticles exhibited low toxicity against MCF-7 cells and slower cell growth compared to curcumin alone which rapidly enhanced the cell growth indicated by the viability of cells compared to the control untreated cells. The applied curcumin concentrations were adjusted according to the loaded curcumin concentration during $CeO_2$/Hal/Cur preparation, the $CeO_2$/Hal had enhanced the functionality of curcumin and reduced its color-background but was not able to inhibit the cancer cells growth. The cellular images are highly demonstrated the efficacy of $CeO_2$/Silica/Cp/Cur in delivering cisplatin in comparison to the untreated control cells where the morphological changes and reduction in cell numbers were detected at both 200 and 400 μg/mL.

Kinetic Models

Different kinetic models were examined and plotted in order to determine the kinetic of the drug release. The kinetic models which were examined are zero order, first order, Hixson-Crowell, Higuchi and Korsmeyer-Peppas, and they were compared with each other by evaluating the regression correlation coefficient value ($R^2$) which describes the relationship between the predicted and actual value, therefore, the closer value of $R^2$ to 1, the better model.

The zero-order model describes the drug releasing from carriers which followed by the equation below, where $Q_0$ is the initial amount of drug, $Q_t$ is the amount of drug at time (t) and $k_0$ is the zero-order rate constant.

$$Q_t = Q_0 + k_t t$$

In the first order model, the drug release depends on its concentration, therefore, the equation below describes it. Where, $C_0$ is the initial concentration, $C_t$ is the concentration at time (t) and k is the first order rate constant.

$$\log(C_t) = \log(C_t) - \frac{-k}{2.303} t$$

In the Hixson-Crowell model, the drug release depends on the surface area of the particles which is proportional to the cube root of the particles volume, and can be described using the equation below. Where, $W_0$ is the initial amount of drug in the carrier, $W_t$ is the amount of drug remains in the carrier at time (t) and $\kappa$ (kappa) is the surface area and volume relationship constant.

$$W_0^{1/3} - (-W_t^{1/3}) = \kappa t$$

The Higuchi model is expressed by considering a few assumptions which are: One dimension and constant drug diffusion, drug molecules are too small compared to the thickness, the initial concentration of the drug is very high compared to the solubility and dissolution of the carrier is negligible. The equation below describes the model, where $Q_t$ is the amount of drug release at time (t) and $k_H$ is the Higuchi dissolution constant.

$$Q_t = k_H \times t^{1/2}$$

Korsmeyer-Peppas model considers both Fickian and non-Fickian drug release mechanisms, and is described by the equation below. Where, $M_t/M_\infty$ is the amount of drug released at time (t), k is the release rate constant and n is the release exponent which indicates the type of release mechanism. If n is equal to 0.45, it indicates the Fickian mechanism, but if it is in the range between 0.45 and 0.89, it indicates non-Fickian mechanism. Moreover, if n is equal to 0.89, it indicates the relaxation transport, but if it is greater than that it indicates the carriage. Therefore, all the mechanisms were examined by choosing four values of n which are 0.45, 0.65, 0.89 and 0.95.

$$\frac{M_t}{M_\infty} = kt^n$$

The best kinetic model was found to be Korsmeyer and Pappas n=0.45 and also it is similar to the Higuchi model. See Table 4 below.

TABLE 4

| | | | | | | | | |
|---|---|---|---|---|---|---|---|---|
| | | Kinetic models | | | | | | |
| Catalyst | Zero order | First order | Hixson-Crowell | Higuchi | Korsmeyer-Peppas n = 0.45 | Korsmeyer-Peppas n = 0.65 | Korsmeyer-Peppas n = 0.89 | Korsmeyer-Peppas n = 0.95 |
| 5 wt % Ce/Spherical silica | 0.8773 | 0.7567 | 0.8798 | 0.9190 | 0.9100 | 0.9235 | 0.8963 | 0.8863 |
| 5 wt % Ce/Hydroxyapetite | 0.6759 | 0.5129 | 0.6834 | 0.8520 | 0.8687 | 0.7969 | 0.7115 | 0.6918 |
| 5 wt % Ce/SiMCM-41 | 0.9302 | 0.7388 | 0.9323 | 0.9534 | 0.9467 | 0.9572 | 0.9412 | 0.9353 |
| 5 wt % Ce/SiSBA-16 | 0.2380 | 0.4985 | 0.9046 | 0.8257 | 0.8089 | 0.8610 | 0.8948 | 0.9009 |
| 5 wt % Ce-EG-Clay | 0.6384 | 0.3582 | 0.6517 | 0.8432 | 0.8696 | 0.7704 | 0.6753 | 0.6547 |
| 5 wt % Ce/Clay nanopowder | 0.7596 | 0.4954 | 0.7697 | 0.9150 | 0.9292 | 0.8676 | 0.7921 | 0.7742 |
| insitu CeSpM41 | 0.7137 | 0.5054 | 0.7202 | 0.8734 | 0.8857 | 0.8269 | 0.7479 | 0.7290 |
| 5 wt % Ce-EG-Halloysite | 0.5667 | 0.4241 | 0.5306 | 0.6679 | 0.6802 | 0.6318 | 0.5842 | 0.5743 |

PEGylation: 5 wt Ce/Hal/Cp

For PEGylation, 14 µl of PEG (Molecular weight=400) was added in 3 ml of deionized water, stirred for 20 min under argon atmosphere, then 150 mg of 5 wt Ce/Hal/Cp was added and stirred under ice cool environment for 24 h. Then the solution mixture was freeze dried using lyophilization technique.

Drug Delivery Study:

The release trend of Cp was studied using dialysis membrane technique. Prior to the study, the dialysis membrane (12 KDa, Sigma Aldrich) was activated and then 15 mg of nanoformulation was dispersed in 25 ml of PBS solution (pH 3 and 6.6). The release of Cp was studied at 37° C. At regular time interval, 5 ml of solution was withdrawn, and release was measured using UV-visible spectroscopy. The withdrawn solution (5 ml) was replaced with equal volume of fresh PBS solution.

Figure 13:
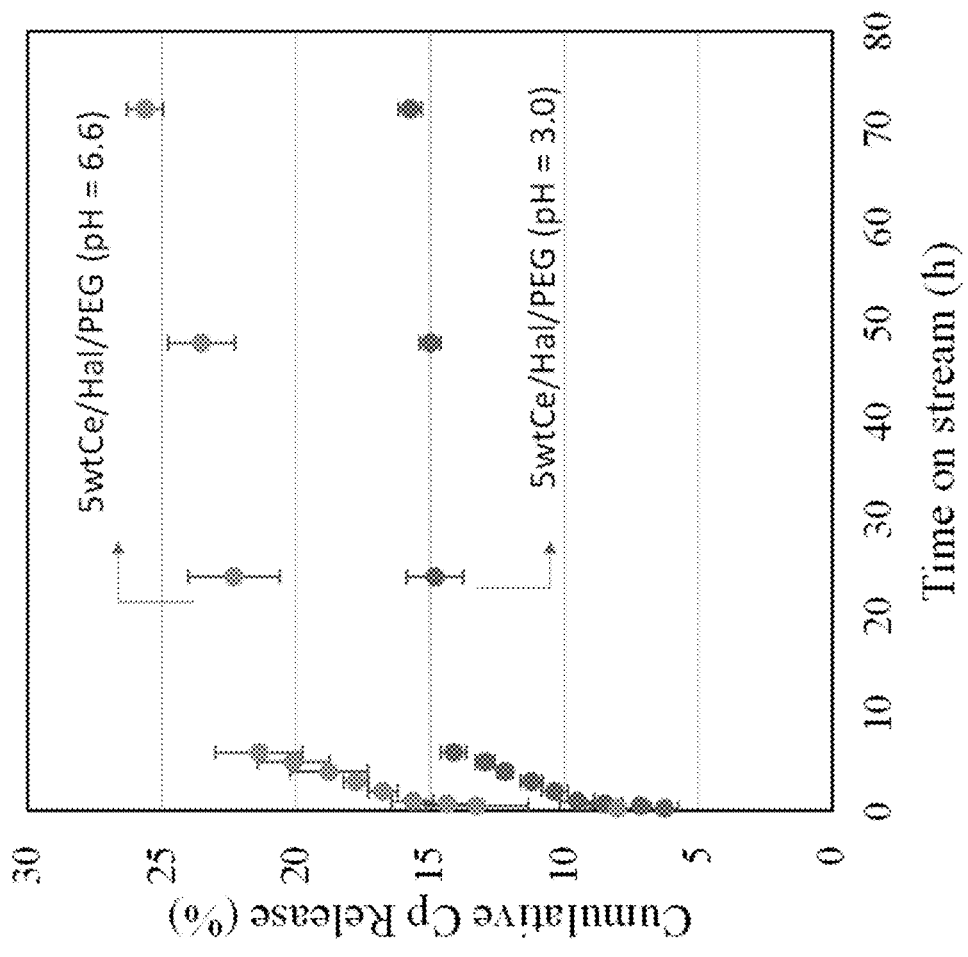
FIG. 13 is a plot of the pH sensitive drug release capability of 5 wt Ce/Hal/PEG/Cp studied using dialysis membrane technique.

The release profile of 5 wt Ce/Hal/PEG/Cp at two different pH conditions is shown in FIG. 13. The stomach cavity is acidic in the pH range is 1-3 and tumor acidic pH range of 6.6. The nanocomposite after pegylation exhibits the high Cp release at tumor microenvironment than acidic stomach condition, while protected from degradation at gastrointestinal tract environment.

The invention claimed is:

1. A method for treating a cancer in a subject, comprising administering to a subject in need thereof a pharmaceutical composition comprising a nanomedicinal composition, comprising
   a nanocarrier comprising:
   a porous silicate and/or aluminosilicate matrix which is at least one selected from the group consisting of particles of mesoporous silica and halloysite nanotubes; and
   cerium oxide nanoparticles having a mean particle size of 1 to 20 nm disposed on the porous silicate and/or aluminosilicate matrix; and a pharmaceutical agent mixture comprising a platinum (II) complex and an antioxidant, the pharmaceutical agent mixture being disposed in the pores and/or on a surface of the nanocarrier, wherein the nanocarrier has a surface area of 15 to 80 m²/g;

the nanocarrier is substantially free of silanes and organosilicates, and the cancer is at least one selected from the group consisting of breast cancer, colorectal cancer, and lung cancer.

2. The method of claim 1, wherein the cancer is a breast cancer.

3. The method of claim 1, wherein the particles of mesoporous silica are substantially spherical and have a mean particle size of 50 to 110 nanometer (nm).

4. The method of claim 1, wherein the porous silicate and/or aluminosilicate matrix is particles of mesoporous silica and the nanocarrier has a surface area of 15 to 45 m²/g, a pore volume of 0.05 to 0.25 cm³/g, and a mean pore size of 14 to 30 nm.

5. The method of claim 1, wherein the halloysite nanotubes have a mean nanotube outer diameter of 10 to 125 nm and a mean nanotube length of 0.25 to 7.5 μm.

6. The method of claim 1, wherein the porous silicate and/or aluminosilicate matrix is halloysite nanotubes and the nanocarrier has a surface area of 40 to 80 m²/g, a pore volume of 0.15 to 0.37 cm³/g, and a mean pore size of 10 to 22 nm.

7. The method of claim 1, wherein the cerium oxide nanoparticles are present in an amount of 1 to 10 wt % based on a total weight of the nanocarrier.

8. The method of claim 1, wherein the platinum (II) complex is at least one selected from the group consisting of cisplatin, carboplatin, and oxaliplatin.

9. The method of claim 8, wherein the platinum (II) complex is cisplatin.

10. The method of claim 1, wherein the antioxidant is at least one selected from the group consisting of quercetin, rutin, coenzyme Q10, gallic acid and curcumin.

11. The method of claim 10, wherein the antioxidant is curcumin.

12. The method of claim 1, wherein the pharmaceutical agent mixture has a weight ratio of the antioxidant to the platinum (II) complex of 1:1 to 10:1.

13. The method of claim 1, wherein the pharmaceutical agent mixture is present in the nanomedicinal composition in an amount of 5 to 50 wt %, based on a total weight of nanomedicinal composition.

14. The method of claim 1, wherein the nanomedicinal composition releases greater than 15% of a total weight of platinum (II) complex within 6 to 12 hours of contact with a suitable biological medium.

15. The method of claim 1, wherein the nanomedicinal composition is formed by:

mixing a cerium salt with the porous silicate and/or aluminosilicate matrix to form a powdery mixture;

calcining the powdery mixture to form the nanocarrier;

mixing the nanocarrier and the antioxidant in an impregnation solution thereby forming an antioxidant-loaded nanocarrier; and mixing the antioxidant-loaded nanocarrier and the platinum (II) complex in an aqueous solution thereby forming the nanomedicinal composition.

16. The method of claim 15, wherein the calcining is performed at a temperature of 200 to 500° C. for 1 to 10 hours.

17. The method of claim 15, wherein the impregnation solution comprises an alcohol having 1 to 5 carbon atoms and the antioxidant is present in an amount of 1 to 7.5 mg/mL of impregnation solution.

18. The method of claim 15, wherein the aqueous solution is a saline and the platinum (II) complex is present in the aqueous solution at a concentration of 0.5 to 5 mg/mL of aqueous solution.

* * * * *